United States Patent
Bednarek

(10) Patent No.: US 9,714,277 B2
(45) Date of Patent: Jul. 25, 2017

(54) PEGYLATED GLUCAGON AND GLP-1 CO-AGONISTS FOR THE TREATMENT OF OBESITY

(71) Applicant: MedImmune Limited, Cambridge (GB)

(72) Inventor: Maria Bednarek, Cambridge (GB)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 14/775,074

(22) PCT Filed: Mar. 13, 2014

(86) PCT No.: PCT/EP2014/055034
§ 371 (c)(1),
(2) Date: Sep. 11, 2015

(87) PCT Pub. No.: WO2014/140222
PCT Pub. Date: Sep. 18, 2014

(65) Prior Publication Data
US 2016/0017016 A1    Jan. 21, 2016

Related U.S. Application Data

(60) Provisional application No. 61/783,675, filed on Mar. 14, 2013.

(51) Int. Cl.
*A61K 38/26* (2006.01)
*C07K 14/605* (2006.01)
*A61K 47/48* (2006.01)
*A61K 38/00* (2006.01)
*A61K 9/00* (2006.01)

(52) U.S. Cl.
CPC ............ *C07K 14/605* (2013.01); *A61K 38/26* (2013.01); *A61K 47/48038* (2013.01); *A61K 47/48215* (2013.01); *A61K 9/0019* (2013.01); *A61K 38/00* (2013.01)

(58) Field of Classification Search
None
See application file for complete search history.

(56) References Cited

U.S. PATENT DOCUMENTS

2009/0202497 A1 *    8/2009   Habener ................ A61K 38/26
424/93.7

FOREIGN PATENT DOCUMENTS

| EP | 0154316 | | 9/1985 |
| EP | 01401384 A1 | | 12/1990 |
| EP | 2173890 | | 3/2011 |
| WO | WO 2011/143209 A1 | | 11/2010 |
| WO | WO 2010/148089 A1 | | 12/2010 |
| WO | WO2010148089 | * | 12/2010 |
| WO | WO 2012/054822 | * | 4/2012 |
| WO | WO 2014/091316 | * | 6/2014 |

OTHER PUBLICATIONS

Correa et al. ('A graph-structural method for prediction of polymer properties' Brazilian Journal of Chemical Engineering v21(4) Oct.-Dec. 2004 pp. 621-628).*
Gao et al. ('Expression, purification, and c-terminal site-specific PEGylation of cysteine-mutated glucagon-like peptide-1' Appl. Biochem. Biotechnol. 2010 v162 pp. 155-165).*
Chae, S.Y., et al., "The fatty acid conjugated exendin-4 analogs for type 2 antidiabetic therapeutics", Journal of Controlled Release, Elsevier, Amsterdam, NL, vol. 14, No. 1, pp. 10-16, May 21, 2010.
International search report and written opinion for PCT Application No. PCT/EP2014/055034, mailed on Jul. 23, 2014.
International Preliminary Report on Patentability in International Application No. PCT/EP2014/055034, issued Sep. 15, 2015.
Written Opinion for International Application No. PCT/EP2014/055034, mailed Sep. 14, 2015.
Merrifield, R.B., et al., "Solid Phase Peptide Synthesis. I. The Synthesis of a Tetrapeptide," Journal of the American Chemical Society, vol. 85 (14), pp. 2149-2154, Jul. 1963.
Baggio, L.L., et al., "A Recombinant Human Glucagon-Like Peptide (GLP)-1-Albumin Proteing (Albugon) Mimics Peptidergic Activation of GLP-1 Receptor-Dependent Pathways Coupled with Satiety, Gastrointestinal Motility, and Glucose Homeostasis", Diabetes, vol. 53, pp. 2492-2500, Sep. 2004.
Barrington, P. et al., LY2189265, a long-acting glucagon-like peptide-1 analogue, showed a dose-dependent effect on insulin secretion in healthy subjects, Diabetes, Obesity and Metabolism, 13, pp. 434-438, 2011.
Paulik, P., et al., Poster 1946, American Diabetes Association, 2012.
Schellenberger, V., et al., "A recombinant polypeptide extends the in vivo half-life of peptides and proteins in a tunable manner," Nature Biotechnology, 27, pp. 1186-1190, Nov. 15, 2009.
Dennis, M.S., et al., "Albumin Binding as a General Strategy for Improving the Pharmacokinetics of Proteins," The Journal of Biology Chemistry, vol. 277, No. 38, pp. 35035-35043, 2002.
Walker, A. et al., "Anti-serum albumin domain antibodies in the development of highly potent, efficacious and long-acting interferon," Protein Engineering, Design & Selection, vol. 23, No. 4, pp. 271-278, 2010.

* cited by examiner

*Primary Examiner* — Karlheinz R Skowronek
*Assistant Examiner* — Ronald Niebauer

(57) ABSTRACT

This disclosure provides pegylated GLP-1/glucagon agonist peptides for the treatment of metabolic diseases, e.g., obesity.

6 Claims, No Drawings

PEGYLATED GLUCAGON AND GLP-1 CO-AGONISTS FOR THE TREATMENT OF OBESITY

CROSS-REFERENCE TO RELATED APPLICATIONS

This application is a U.S. National Stage Application of International Application No. PCT/EP2014/055034, filed on Mar. 13, 2014, said International Application No. PCT/EP2014/055034 claims benefit under 35 U.S.C. §119(e) of the U.S. Provisional Application No. 61/783,675, filed on Mar. 14, 2013. Each of the above listed applications is incorporated by reference herein in its entirety for all purposes.

REFERENCE TO SEQUENCE LISTING SUBMITTED ELECTRONICALLY

The content of the electronically submitted sequence listing in ASCII text file (Name: GLPGG101WO_ST25; Size: 44.6 kilobytes; and Date of Creation: Mar. 10, 2014) filed with the application is incorporated herein by reference in its entirety.

BACKGROUND

Obesity is a major and growing health problem worldwide, and is associated with many life-threatening diseases such as cardiovascular disease, renal disease, hypertension, stroke, infertility, respiratory dysfunction, and type 2 diabetes.

Glucagon and glucagon-like peptide-1 (GLP-1) derive from pre-proglucagon, a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of proglucagon (53 to 81 of preproglucagon), while GLP-1 is produced as a 37-amino acid peptide that corresponds to amino acids 72 through 108 of proglucagon (92 to 128 of preproglucagon). GLP-1(7-36) amide or GLP-1(7-37) acid are biologically active forms of GLP-1, that demonstrate essentially equivalent activity at the GLP-1 receptor.

Glucagon is produced by the pancreas and interacts with the glucagon receptor ("glucR"). Glucagon acts in the liver to raise blood glucose via gluconeogenesis and glycogenolysis. When blood glucose begins to fall, glucagon signals the liver to break down glycogen and release glucose, causing blood glucose levels to rise toward a normal level.

GLP-1 has different biological activities compared to glucagon. It is secreted from gut L cells and binds to the GLP-1 receptor. Its activities include stimulation of insulin synthesis and secretion, inhibition of glucagon secretion, and inhibition of food intake.

Both glucagon and GLP-1, acting as agonists at their respective receptors, have been shown to be effective in weight loss. Certain GLP-1 analogs are being sold or are in development for treatment of obesity including, e.g., Liraglutide (VICTOZA® from Novo Nordisk) and Exenatide (Byetta® from Eli Lilly/Amylin).

There remains a need for more agents for effective treatment of obesity, for example, GLP-1/Glucagon agonist peptides with improved solubility, formulatability, stability, and efficacy.

BRIEF SUMMARY

This disclosure provides an isolated peptide comprising or consisting of the amino acid sequence:

```
                                        (SEQ ID NO: 2)
HX₁X₂GT FTSDX₃ SX₄X₅X₆X₇X₈X₉X₁₀AX₁₁ X₁₂FVX₁₃W

X₁₄X₁₅X₁₆
``` where $X_1$ is S, G, alpha-amino-iso-butyric acid; $X_2$ is Q or E; $X_3$ is Y of K(PEG4palm); $X_4$ is E, R or K(PEG4palm); $X_5$ is Y or K(PEG4palm); $X_6$ is L or K(PEG4palm); $X_7$ is D or E; $X_8$ is S, E or K(PEG4palm); $X_9$ is R, E, S, or K(gEpalm), K(PEG2palm), K(PEG3palm), K(PEG4palm) or K(PEG2-PEG2-gEpalm); $X_{10}$ is R, A, or K(gEpalm), K(PEG4palm); $X_{11}$ is Q, R, A, E or K(gEpalm), K(PEG4palm); $X_{12}$ is D or K(gEpalm); $X_{13}$ is Q, A or E; $X_{14}$ is L or E; $X_{15}$ is V or E; and $X_{16}$ is absent or A (SEQ ID NO:2); wherein only one amino acid is palmitoylated per molecule.

In certain embodiments of the peptides described above, the carboxyl group of $X_{15}$ or $X_{16}$ is pegylated. In some embodiments the PEG group is a polyethylene glycol oligomer of 2, 3, 4, 5, 6, 7, 8, 9, 10, 11 or 12 units. In some embodiments, the $X_{15}$ amino acid is conjugated at the carboxyl end to 6-aminohexanoic acid or 11-aminoundecanoic acid and $X_{16}$ is absent.

In certain embodiments, the isolated peptide comprises an amino acid sequence selected from the group consisting of:

```
                               (SEQ ID NO: 3)
HSQGTFTSDYSKYLDSRRAQDFVQWLV (SEQ ID NO: 18)
HSQGTFTSDYSKYLDSRRAQDFVQWLE (SEQ ID NO: 4)
HSQGTFTSDYSKYLDKSRARDFVAWLV (SEQ ID NO: 5)
HSQGTFTSDYSKYLDKRRAQDFVQWEV (SEQ ID NO: 6)
HSQGTFTSDYSKYLDKRRAQDFVQWLE (SEQ ID NO: 7)
HSQGTFTSDYSKYLDEKRAQDFVQWLV (SEQ ID NO: 76)
HSQGTFTSDYSKYLDSKRAQDFVQWLV (SEQ ID NO: 77)
HSQGTFTSDYSKYLDSKRARDFVAWLV (SEQ ID NO: 78)
HSQGTFTSDYSKYLDSKRARDFVAWLE (SEQ ID NO: 79)
HSQGTFTSDYSKYLDSKRAQDFVQWLE (SEQ ID NO: 80)
HSQGTFTSDYSKYLDSKRAQDFVQWEV (SEQ ID NO: 81)
HSQGTFTSDKSKYLDSSRARDFVAWLV (SEQ ID NO: 82)
```

```
HSQGTFTSDYSKYLDSRKAQDFVQWLE (SEQ ID NO: 3)
HSQGTFTSDYSKYLDSRRAQDFVQWLV (SEQ ID NO: 83)
HSQGTFTSDYSKKLDSSRARDFVAWLV (SEQ ID NO: 84)
HSQGTFTSDYSEYLDSKRAQDFVQWLV (SEQ ID NO: 85)
HSQGTFTSDYSEYLDSKRAADFVQWLV (SEQ ID NO: 86)
HSQGTFTSDYSRYLDSKRARDFVAWLV (SEQ ID NO: 87)
HSQGTFTSDYSKYLDSKRAQDFVAWLV (SEQ ID NO: 76)
HSQGTFTSDYSKYLDSKRAQDFVQWLV (SEQ ID NO: 88)
HSQGTFTSDYSKYKDSRRAQDFVQWLV (SEQ ID NO: 89)
HSQGTFTSDYSKYKDEERAQDFVQWLV (SEQ ID NO: 90)
HSQGTFTSDYSKYKDSSRARDFVAWLV (SEQ ID NO: 14)
HSQGTFTSDYSKYLDSERARDFVAWLV (SEQ ID NO: 91)
HSQGTFTSDYSKYLDKRRAQDFVQWLV (SEQ ID NO: 6)
HSQGTFTSDYSKYLDKRRAQDFVQWLE (SEQ ID NO: 5)
HSQGTFTSDYSKYLDKRRAQDFVQWEV (SEQ ID NO: 92)
HSQGTFTSDYSKYLDSRKAQDFVQWLV (SEQ ID NO: 93)
HSQGTFTSDYSKYLDSRRAKDFVQWLV (SEQ ID NO: 94)
HSQGTFTSDYSKYLDSERAKDFVAWLV (SEQ ID NO: 95)
HSQGTFTSDYSKYLDSRRAQKFVQWLV (SEQ ID NO: 96)
HSEGTFTSDYSKYKDSRRAQDFVQWLV (SEQ ID NO: 97)
HSEGTFTSDYSKYLDSKRAQDFVQWLV (SEQ ID NO: 98)
HGQGTFTSDYSKYLDSKRAQDFVQWLV (SEQ ID NO: 99)
HGQGTFTSDYSKYLDSKRAEDFVQWLV (SEQ ID NO: 100)
HGQGTFTSDYSKYLDSKRAQDFVEWLV (SEQ ID NO: 101)
HGQGTFTSDYSKYLDSEKARDFVAWLV (SEQ ID NO: 102)
HGQGTFTSDYSEYLDSKRAQDFVQWLV (SEQ ID NO: 103)
HGQGTFTSDYSRYLDSKRARDFVEWLV (SEQ ID NO: 104)
HGQGTFTSDYSEYLDSKRARDFVEWLV (SEQ ID NO: 105)
HGQGTFTSDYSKYKDSRRAQDFVQWLV (SEQ ID NO: 106)
HGQGTFTSDYSKYLESKRAQDFVQWLV (SEQ ID NO: 107)
HX₁QGTFTSDYSKYLDSKRAQDFVAWLV (SEQ ID NO: 108)
HX₁QGTFTSDYSKYLDSKRAQDFVQWLV (SEQ ID NO: 109)
HX₁QGTFTSDYSKYKDSERARDFVAWLV (SEQ ID NO: 110)
HSQGTFTSDYSKYLDSKRAQDFVQWLEA
``` wherein:

$X_1$ is alpha-amino-iso-butyric acid;

when the amino acid at position 10, 13, 14, 16, 17, 18, 20 or 21 is palmitoylated lysine, then the lysine at position 12 is not palmitoylated;

when the amino acid at position 10, 13, 14, 16, 17, 18, 20 and 21 is not a palmitoylated lysine, then the lysine at position 12 is optionally palmitoylated; and wherein the peptide is pegylated at the C-terminal amino acid with a (PEG)$x^2$ group, wherein $x^2$ is 2-12.

In some embodiments, the peptide comprises a lysine that is palmitoylated with a palmitoyl group on the N (epsilon) group of said lysine residue. In some embodiments, the palmitoyl group is linked to the lysine via a linker. The linker may be, for example, a gamma glutamate linker or a polyethylene glycol (PEG) linker.

In some embodiments, the PEG linker is, for example, a PEG$_2$, PEG$_3$, PEG$_4$, (PEG)$_2$-gE, (PEG)$_4$-gE, or (PEG)$_2$-(PEG)$_2$-gE linker.

In some embodiments, the peptide comprises the amino acid sequence of:

```
                               (SEQ ID NO: 3)
HSQGTFTSDYSKYLDSRRAQDFVQWLV(PEG)₂

(SEQ ID NO: 3)
HSQGTFTSDYSKYLDSRRAQDFVQWLV(PEG)₄

(SEQ ID NO: 8)
HSQGTFTSDYSBYLDSRRAQDFVQWLV(PEG)₄

(SEQ ID NO: 9)
HSQGTFTSDYSB₁YLDSRRAQDFVQWLV(PEG)₄

(SEQ ID NO: 10)
HSQGTFTSDYSKYBDSRRAQDFVQWLV(PEG)₄

(SEQ ID NO: 11)
HGQGTFTSDYSKYBDSRRAQDFVQWLV(PEG)₄

(SEQ ID NO: 12)
HSEGTFTSDYSKYBDSRRAQDFVQWLV(PEG)₄

(SEQ ID NO: 13)
HSQGTFTSDYSKYBDEERAQDFVQWLV(PEG)₄

(SEQ ID NO: 14)
HSQGTFTSDYSKYLDSERARDFVAWLV(PEG)₄

(SEQ ID NO: 15)
HX₁QGTFTSDYSKYBDSERARDFVAWLV(PEG)₄

(SEQ ID NO: 16)
HSQGTFTSDYSKYLDBRRAQDFVQWLV(PEG)₄
```

```
                                                      (SEQ ID NO: 17)
HSQGTFTSDYSKYLDB₁RRAQDFVQWLV(PEG)₄

(SEQ ID NO: 18)
HSQGTFTSDYSKYLDSRRAQDFVQWLE(PEG)₄

(SEQ ID NO: 19)
HSQGTFTSDYSKYLDB₁RRAQDFVQWLE(PEG)₄

(SEQ ID NO: 20)
HSQGTFTSDYSKYLDBRRAQDFVQWEV(PEG)₄

(SEQ ID NO: 21)
HSQGTFTSDYSKYLDB₁RRAQDFVQWEV(PEG)₄

(SEQ ID NO: 22)
HSQGTFTSDYSKYLDSRBAQDFVQWLV(PEG)₄

(SEQ ID NO: 23)
HSQGTFTSDYSKYLDSRB₁AQDFVQWLV(PEG)₄

(SEQ ID NO: 24)
HGQGTFTSDYSKYLDSEBARDFVAWLV(PEG)₄

(SEQ ID NO: 25)
HSQGTFTSDYSKYLDSRRABDFVQWLV(PEG)₄

(SEQ ID NO: 26)
HSQGTFTSDYSKYLDSRRAB₁DFVQWLV(PEG)₄

(SEQ ID NO: 27)
HSQGTFTSDYSKYLDSERABDFVAWLV(PEG)₄

(SEQ ID NO: 28)
HSQGTFTSDYSKYLDSRRAQBFVQWLV(PEG)₄

(SEQ ID NO: 29)
HSQGTFTSDYSKYLDSRAAQBFVQWLV(PEG)₄

(SEQ ID NO: 30)
HSQGTFTSDB₁SKYLDSSRARDFVAWLV(PEG)₄

(SEQ ID NO: 31)
HSQGTFTSDYSKB₁LDSSRARDFVAWLV(PEG)₄

(SEQ ID NO: 32)
HSQGTFTSDYSKYB₁DSRRAQDFVQWLV(PEG)₄

(SEQ ID NO: 33)
HSQGTFTSDYSKYB₁DSSRARDFVAWLV(PEG)₄

(SEQ ID NO: 34)
HSQGTFTSDYSKYLDB₁SRARDFVAWLV(PEG)₄

(SEQ ID NO: 35)
HSQGTFTSDYSKYLDSBRAQDFVQWLV(PEG)₄

(SEQ ID NO: 36)
HSQGTFTSDYSKYLDSRB₁RAQDFVQWLV(PEG)₄

(SEQ ID NO: 37)
HSQGTFTSDYSKYLDSB₂RAQDFVQWLV(PEG)₄

(SEQ ID NO: 38)
HSQGTFTSDYSKYLDSB₃RAQDFVQWLV(PEG)₄

(SEQ ID NO: 39)
HSQGTFTSDYSEYLDSBRAQDFVQWLV(PEG)₄

(SEQ ID NO: 40)
HGQGTFTSDYSEYLDSBRARDFVEWLV(PEG)₄

(SEQ ID NO: 41)
HX₁QGTFTSDYSKYLDSBRAQDFVQWLV(PEG)₄

(SEQ ID NO: 42)
HX₁QGTFTSDYSKYLDSB₁RAQDFVQWLV(PEG)₄

(SEQ ID NO: 43)
HGQGTFTSDYSKYLDSBRAQDFVQWLV(PEG)₄

(SEQ ID NO: 44)
HGQGTFTSDYSKYLDSB₁RAQDFVQWLV(PEG)₄

(SEQ ID NO: 45)
HSQGTFTSDYSEYLDSBRAADFVQWLV(PEG)₄

(SEQ ID NO: 46)
HGQGTFTSDYSRYLDSBRARDFVEWLV(PEG)₄

(SEQ ID NO: 47)
HSQGTFTSDYSKYLDSBRAQRDFVAWLV(PEG)₁₂

(SEQ ID NO: 48)
HSQGTFTSDYSRYLDSBRARDFVAWLV(PEG)₄

(SEQ ID NO: 49)
HSQGTFTSDYSEYLDSBRARDFVAWLV(PEG)₄

(SEQ ID NO: 50)
HSQGTFTSDYSKYLDSBRARDFVAWLV(PEG)₄

(SEQ ID NO: 51)
HSQGTFTSDYSKYLDSB₆RAQDFVQWLE(PEG)₄

(SEQ ID NO: 52)
HSQGTFTSDYSKYLDSB₅RAQDFVQWLV(PEG)₄

(SEQ ID NO: 53)
HSQGTFTSDYSKYLDSB₄RAQDFVQWLV(PEG)₄

(SEQ ID NO: 54)
HX₁QGTFTSDYSKYLDSBRAQDFVAWLV(PEG)₄

(SEQ ID NO: 55)
HX₁QGTFTSDYSKYLDSBRARDFVAWLV(PEG)₄

(SEQ ID NO: 56)
HX₁QGTFTSDYSKYLDSB₄RARDFVAWLV(PEG)₄

(SEQ ID NO: 57)
HSEGTFTSDYSKYLDSBRAQDFVQWLV(PEG)₄

(SEQ ID NO: 58)
HSEGTFTSDYSKYLDSB₁RAQDFVQWLV(PEG)₄

(SEQ ID NO: 59)
HGQGTFTSDYSKYLESBRAQDFVQWLV(PEG)₄

(SEQ ID NO: 60)
HGQGTFTSDYSEYLDSBRAQDFVQWLV(PEG)₄

(SEQ ID NO: 61)
HGQGTFTSDYSKYLESB₁RAQDFVQWLV(PEG)₄

(SEQ ID NO: 62)
HGQGTFTSDYSKYLDSBRAEDFVQWLV(PEG)₄

(SEQ ID NO: 63)
HGQGTFTSDYSKYLDSBRAQDFVEWLV(PEG)₄

(SEQ ID NO: 43)
HGQGTFTSDYSKYLDSBRAQDFVQWLV(PEG)₂

(SEQ ID NO: 43)
HGQGTFTSDYSKYLDSBRAQDFVQWLV(PEG)₃

(SEQ ID NO: 43)
HGQGTFTSDYSKYLDSBRAQDFVQWLV(PEG)₆

(SEQ ID NO: 64)
HSQGTFTSDYSKYLDEBRAQDFVQWLV(PEG)₄

(SEQ ID NO: 65)
HSQGTFTSDYSKYLDSB₁RAQDFVQWLV(PEG)₂

(SEQ ID NO: 65)
HSQGTFTSDYSKYLDSB₁RAQDFVQWLV(PEG)₃

(SEQ ID NO: 65)
HSQGTFTSDYSKYLDSB₁RAQDFVQWLV(PEG)₆
```

-continued

HSQGTFTSDYSKYLDSB$_1$RAQDFVQWLV(PEG)$_8$ (SEQ ID NO: 65)

HSQGTFTSDYSKYLDSB$_1$RAQDFVQWLV(PEG)$_{12}$ (SEQ ID NO: 65)

HSQGTFTSDYSKYLDSBRAQDFVQWLE(PEG)$_4$ (SEQ ID NO: 66)

HSQGTFTSDYSKYLDSB$_3$RAQDFVQWLE(PEG)$_4$ (SEQ ID NO: 67)

HSQGTFTSDYSKYLDSB$_2$RAQDFVQWLE(PEG)$_4$ (SEQ ID NO: 68)

HSQGTFTSDYSKYLDSB$_1$RAQDFVQWLE(PEG)$_4$ (SEQ ID NO: 69)

HGQGTFTSDYSKYLDSBRAQDFVQWLE(PEG)$_4$ (SEQ ID NO: 70)

HSQGTFTSDYSKYLDSBRAQDFVQWLEA(PEG)$_4$ (SEQ ID NO: 66)

HSQGTFTSDYSKYLDSBRAQDFVQWEV(PEG)$_4$ (SEQ ID NO: 71)

HSQGTFTSDYSKYLDSB$_1$RAQDFVQWEV(PEG)$_4$ (SEQ ID NO: 72)

HSQGTFTSDYSKYLDSBRAQDFVQWLV(PEG)$_2$ (SEQ ID NO: 35)

HSQGTFTSDYSKYLDSRBAQDFVQWLE(PEG)$_4$ (SEQ ID NO: 73)

HSQGTFTSDYSKYLDSRB$_1$AQDFVQWLE(PEG)$_4$ (SEQ ID NO: 74)

HSQGTFTSDYSKYLDB$_1$RRAQDFVQWEV(PEG)$_4$ (SEQ ID NO: 21)

HSQGTFTSDYSKYLDB$_1$RRAQDFVQWLE(PEG)$_4$ (SEQ ID NO: 19)

HSQGTFTSDYSKYLDSB$_4$RARDFVAWLE(PEG)$_2$ (SEQ ID NO: 75)

wherein:
X$_1$ is alpha-amino-iso-butyric acid;
B is K(gE-palm);
B$_1$ is K(PEG4-palm);
B$_2$ is K(PEG3-palm);
B$_3$ is K(PEG2-palm);
B$_4$ is K(PEG4-gE-palm);
B$_5$ is K(PEG2-gE-palm); and
B$_6$ is K(PEG2-PEG2-gE-palm).

An isolated peptide wherein said peptide comprises the amino acid sequence of:

HSQGTFTSDYSKYLDSRRAQDFVQWLV (SEQ ID NO: 3)
or
HSQGTFTSDYSKYLDSRRAQDFVQWLE, (SEQ ID NO: 18)

and wherein said peptide is conjugated at the C-terminus to either 6-aminohexanoic acid or 11-aminoundecanoic acid.

The invention also provides an isolated peptide comprising a GLP-1 activity and a glucagon activity wherein said peptide comprises PEG groups at the C-terminus of the polypeptide and which peptide has an increased potency in serum than the same peptide without the PEG groups.

In some embodiments, the peptide comprises about 2-12 PEG units (abbreviated (PEG)x where x is 2-12, e.g., (PEG)$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$) conjugated to the C-terminus. In some embodiments, the peptide comprises PEG group is a (PEG)x group wherein x is 2-8. In some embodiments, the peptide comprises PEG group is a (PEG)x group wherein x is 2-6. In some embodiments, the peptide comprises PEG group is a (PEG)x group wherein x is 2-4.

In some embodiments, the peptide of the invention has increased GLP1 activity and/or increased stability as compared to the peptide without the PEG group.

In some embodiments peptide binds to a glucagon receptor. In some embodiments, the peptide binds to a GLP-1 receptor. In some embodiments, the peptide binds to both a glucagon receptor and a GLP-1 receptor.

In some embodiments, the glucagon receptor is a mouse glucagon receptor or a human glucagon receptor. In some embodiments, the peptide binds to a human glucagon receptor with an EC50 in the cAMP assay of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM.

In some embodiments, the GLP-1 receptor is a mouse GLP-1 receptor or a human GLP-1 receptor. In some embodiments, the peptide binds to a human GLP-1 receptor with an EC50 in the cAMP assay of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM.

In some embodiments, the peptide is an agonist of GLP-1 activity, an agonist of glucagon activity, or an agonist of both GLP-1 and glucagon activity. In some embodiments, the peptide binds to both a glucagon receptor and a GLP-1 receptor, and exhibits at least about 2-fold, 5-fold, or 10-fold greater activity relative to the natural ligand at the GLP-1 receptor than at the glucagon receptor.

In some embodiments, the peptide of the invention further comprise a heterologous moiety associated with the peptide. The heterologous moiety is a protein, a peptide, a protein domain, a linker, an organic polymer, an inorganic polymer, a polyethylene glycol (PEG), biotin, an albumin, a human serum albumin (HSA), a HSA FcRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, a recombinant polypeptide polymer, a cytokine, or a combination of two or more of the recited moieties.

The invention also provides a pharmaceutical composition comprising the peptide of the invention as described herein and a pharmaceutically acceptable carrier, and a kit comprising such a composition.

The invention also provides a method of increasing the potency of a GLP-1 analog comprising conjugating a PEG group to a GLP-1 analogue wherein said PEG group comprises between 2 and 12 PEG units. In some embodiments, the PEG group comprises between 2 and 8 PEG units. In some embodiments, the PEG group comprises between 2 and 6 PEG units. In some embodiments, the PEG group comprises between 2 and 4 PEG units.

The invention also provides a method of treating or preventing a disease or condition caused or characterized by excess body weight, comprising administering to a subject in need of treatment an effective amount of the peptide of the invention as described herein, or a composition of the invention as described herein.

In some embodiments, the disease or condition is obesity.

In some embodiments of the method of the invention, the peptide is administered by injection. In some embodiments, the injection is administered subcutaneously. In some embodiments, the injection is administered once per day. In some embodiments, the injection is administered once per week. In some embodiments, the subject is human.

The invention further provides a method of reducing body weight in a subject comprising administering to a subject in need of treatment an effective amount of the peptide of the invention as described herein, or a composition of the invention as described herein.

Any of the peptides provided herein can comprise one or more modified amino acids, for example, the addition of an acyl moiety, for example, the modification can be the addition of a palmitoyl moiety on the N (epsilon) group of a lysine residue. In certain embodiments, the palmitoyl group is linked to the lysine residue through a gamma glutamate linker. Alternative linkers have been used including beta alanine, 6-aminohexanoic acid and 11-aminoundecanoic acid. Further alternative linkers are possible including linkers containing PEG moieties for instance containing 2-8 PEG units. In some embodiments, the linkers include short PEG moieties such as 2, 3 or 4 PEG units.

In various embodiments, the isolated peptides provided herein can bind to a glucagon receptor, to a GLP-1 receptor, or to both a glucagon and a GLP-1 receptor. In certain aspects the glucagon receptor is a human glucagon receptor, and or the GLP-1 receptor is a human GLP-1 receptor. In certain aspects an isolated peptide as provided herein binds to a human glucagon receptor with an EC50 in the cAMP assay (as described herein) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain aspects an isolated peptide as provided herein binds to a human GLP-1 receptor with an EC50 in the cAMP assay of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM.

In certain aspects, an isolated peptide as provided herein is an agonist of GLP-1 activity, an agonist of glucagon activity, or an agonist of both GLP-1 and glucagon activity. In some embodiments, an isolated peptide as provided herein binds to both a glucagon receptor and a GLP-1 receptor, and exhibits at least about 2-fold greater activity relative to the natural ligand at the GLP-1 receptor than at the glucagon receptor. In one embodiment the peptide has a 5 to 10 fold higher relative potency at the GLP1R, compared to GLP1, than at the glucagon receptor, relative to glucagon.

In certain aspects, an isolated peptide as provided herein can further comprise a heterologous moiety associated with the peptide. In some aspects, the heterologous moiety is a protein, a peptide, a protein domain, a linker, an organic polymer, an inorganic polymer, a polyethylene glycol (PEG), biotin, an albumin, a human serum albumin (HSA), a HSA FcRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, a recombinant polypeptide polymer, a cytokine, or any combination of two or more of such moieties.

Also provided is a pharmaceutical composition comprising an isolated peptide as described herein, and a carrier. Further provided is a kit including such a pharmaceutical composition.

Also provided is a method for treating or preventing a disease or condition caused or characterized by excess body weight, where the method includes administering to a subject in need of treatment an effective amount of an isolated peptide as provided herein, or a composition which includes such a peptide. In certain aspects, the disease or condition can be obesity, insulin resistance, glucose intolerance, pre-diabetes, increased fasting glucose, type 2 diabetes, hypertension, dyslipidemia (or a combination of these metabolic risk factors), glucagonomas, cardiovascular disease, e.g., congestive heart failure, atherosclerois, arteriosclerosis, coronary heart disease, or peripheral artery disease; stroke, respiratory dysfunction, renal disease, and any combination thereof. According to the method, an isolated peptide as described herein can be administered by injection, e.g., subcutaneous injection. According to the method, the peptide can be administered once per day. In some embodiments, the injection is administered once per week. In certain embodiments, the subject is a human.

Also provided is a method for treating or preventing a disease or condition caused or characterized by excess body weight, where the method includes administering to a subject in need of treatment an effective amount of an isolated peptide as provided herein, or a composition which includes such a peptide. According to the method, an isolated peptide as described herein can be administered by injection, e.g., subcutaneous injection. According to the method, the peptide can be administered once per day. In some embodiments, the injection is administered once per week. In certain embodiments, the subject is a human.

DETAILED DESCRIPTION

Definitions

Throughout this disclosure, the term "a" or "an" entity refers to one or more of that entity; for example, "a polynucleotide," is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

As used herein, the term "polypeptide" is intended to encompass a singular "polypeptide" as well as plural "polypeptides," and comprises any chain or chains of two or more amino acids. Thus, as used herein, a "peptide," a "peptide subunit," a "protein," an "amino acid chain," an "amino acid sequence," or any other term used to refer to a chain or chains of two or more amino acids, are included in the definition of a "polypeptide," even though each of these terms can have a more specific meaning. The term "polypeptide" can be used instead of, or interchangeably with any of these terms. The term further includes polypeptides which have undergone post-translational or post-synthesis modifications, for example, glycosylation, acetylation, phosphorylation, amidation, derivatization by known protecting/blocking groups, proteolytic cleavage, or modification by non-naturally occurring amino acids.

More specifically, the term "peptide" as used herein encompasses a full length peptides and fragments, variants or derivatives thereof, e.g., a GLP-1/glucagon agonist peptide (e.g., 29, 30, or 31 amino acids in length). A "peptide" as disclosed herein, e.g., a GLP-1/glucagon agonist peptide, can be part of a fusion polypeptide comprising additional components such as, e.g., an Fc domain or an albumin domain, to increase half-life. A peptide as described herein can also be derivatized in a number of different ways.

The terms "fragment," "analog," "derivative," or "variant" when referring to a GLP-1/glucagon agonist peptide includes any peptide which retains at least some desirable activity, e.g., binding to glucagon and/or GLP-1 receptors. Fragments of GLP-1/glucagon agonist peptides provided herein include proteolytic fragments, deletion fragments which exhibit desirable properties during expression, purification, and or administration to an subject.

The term "variant," as used herein, refers to a peptide that differs from the recited peptide due to amino acid substitutions, deletions, insertions, and/or modifications. Variants can be produced using art-known mutagenesis techniques. Variants can also, or alternatively, contain other modifications—for example a peptide can be conjugated or coupled, e.g., fused to a heterologous amino acid sequence or other moiety, e.g., for increasing half-life, solubility, or stability. Examples of moieties to be conjugated or coupled to a peptide provided herein include, but are not limited to, albumin, an immunoglobulin Fc region, polyethylene glycol (PEG), and the like. The peptide can also be conjugated or produced coupled to a linker or other sequence for ease of synthesis, purification or identification of the peptide (e.g., 6-His), or to enhance binding of the polypeptide to a solid support.

The term "sequence identity" as used herein refers to a relationship between two or more polynucleotide sequences or between two or more polypeptide sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10), and any other required parameter including but not limited to matrix option.

The terms "composition" or "pharmaceutical composition" refer to compositions containing a GLP-1/glucagon agonist peptide provided herein, along with e.g., pharmaceutically acceptable carriers, excipients, or diluents for administration to a subject in need of treatment, e.g., a human subject being treated for obesity.

The term "pharmaceutically acceptable" refers to compositions that are, within the scope of sound medical judgment, suitable for contact with the tissues of human beings and animals without excessive toxicity or other complications commensurate with a reasonable benefit/risk ratio.

An "effective amount" is that amount of a GLP-1/glucagon agonist peptide provided herein, the administration of which to a subject, either in a single dose or as part of a series, is effective for treatment, e.g., treatment of obesity. An amount is effective, for example, when its administration results in one or more of weight loss or weight maintenance (e.g., prevention of weight gain), loss of body fat, prevention or modulation hypoglycemia, prevention or modulation hyperglycemia, promotion of insulin synthesis, or reduction in food intake. This amount can be a fixed dose for all subjects being treated, or can vary depending upon the weight, health, and physical condition of the subject to be treated, the extent of weight loss or weight maintenance desired, the formulation of peptide, a professional assessment of the medical situation, and other relevant factors.

The term "subject" is meant any subject, particularly a mammalian subject, in need of treatment with a GLP-1/ glucagon agonist peptide provided herein. Mammalian subjects include, but are not limited to, humans, dogs, cats, guinea pigs, rabbits, rats, mice, horses, cattle, bears, cows, apes, monkeys, orangutans, and chimpanzees, and so on. In one embodiment, the subject is a human subject.

As used herein, an "subject in need thereof" refers to an individual for whom it is desirable to treat, e.g., to an obese subject or a subject prone to obesity for whom it is desirable to facilitate weight or body fat loss, weight or body fat maintenance, or to prevent or minimize weight gain over a specified period of time.

As used herein a "GLP-1/glucagon agonist peptide" is a chimeric peptide that exhibits activity at the glucagon receptor of at least about 1%, 5%, 10%, 20%, 30%, 40%, 50%, 60%, 70%, 80%, 90%, 95%, or more relative to native glucagon and also exhibits activity at the GLP-1 receptor of about at least about 1%, 5%, 10%, 20%, 30%, 40%, 50%, 60%, 70%, 80%, 90%, 95%, or more relative to native GLP-1, under the conditions of assay 1.

As used herein the term "native glucagon" refers to naturally-occurring glucagon, e.g., human glucagon, comprising the sequence of SEQ ID NO: 1. The term "native GLP-1" refers to naturally-occurring GLP-1, e.g., human GLP-1, and is a generic term that encompasses, e.g., GLP-1(7-36) amide (SEQ ID NO: 2), GLP-1(7-37) acid (SEQ ID NO: 3) or a mixture of those two compounds. As used herein, a general reference to "glucagon" or "GLP-1" in the absence of any further designation is intended to mean native human glucagon or native human GLP-1, respectively. Unless otherwise indicated, "glucagon" refers to human glucagon, and "GLP-1" refers to human GLP-1.

GLP-1/Glucagon Agonist Peptides

Provided herein are peptides which bind both to a glucagon receptor and to a GLP-1 receptor. In certain embodiments, the peptides provided herein are co-agonists of glucagon and GLP-1 activity. Such peptides are referred to herein as GLP-1/glucagon agonist peptides. GLP-1/glucagon agonist peptides as provided herein possess GLP-1 and glucagon activities with favorable ratios to promote weight loss, prevent weight gain, or to maintain a desirable body weight, and possess optimized solubility, formulatability, and stability. In certain embodiments, GLP-1/glucagon agonist peptides as provided herein are active at the human GLP1 and human glucagon receptors, in certain embodiment relative activity compared to the natural ligand at the GLP-1 receptor is at least about 1-fold, 2-fold 5-fold, 8-fold, 10-fold, 15-fold, 20-fold, or 25-fold higher than at the glucagon receptor.

In certain embodiments, GLP-1/glucagon agonist peptides as disclosed have desirable potencies at the glucagon and GLP-1 receptors, and have desirable relative potencies for promoting weight loss. In certain embodiments, GLP-1/glucagon agonist peptides as disclosed exhibit in vitro potencies at the GLP-1 receptor as shown by an EC50 in the cAMP assay (see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain embodiments, GLP-1/glucagon agonist peptides as disclosed exhibit in vitro potencies at the glucagon receptor as shown by an EC50 in the cAMP assay (see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain embodiments, GLP-1/glucagon agonist peptides as disclosed have relative GLP1-R/glucR potency ratios, when compared to the native ligands, in the range of about 0.01 to 0.50, e.g., from about 0.02 to 0.30, e.g., about 0.02, 0.03, 0.04, 0.05, 0.06, 0.07, 0.08, 0.09, 0.10, 0.11. 0.12, 0.13, 0.14, 0.15, 0.16, 0.17, 0.18, 0.19, 0.20, 0.21, 0.22, 0.23, 0.24, 0.25, 0.26, 0.27, 0.28, or 0.30. when using assay 2.

In certain embodiments, GLP-1/glucagon agonist peptides as disclosed exhibit in vitro potencies at the glucose-dependent insulinotropic peptide (gastric inhibitory peptide) (GIPR) as shown by an EC50 in the cAMP assay (see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM.

In certain embodiments, GLP-1/glucagon agonist peptides provided herein possess one or more criteria of acceptable solubility, ease in formulatability, plasma stability, and improved pharmacokinetic properties. In certain embodiments, GLP-1/glucagon agonist peptides as disclosed are soluble in standard buffers over a broad pH range.

In certain embodiments, GLP-1/glucagon agonist peptides are soluble in common buffer solutions at a concentration up to 0.5 mg/ml, 0.6 mg/ml, 0.7 mg/ml, 0.8 mg/ml, 0.9 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, or more, in buffer systems and a range of ionic strengths, e.g., from 0.25 to 150 mM, including, but not limited to phosphate buffer, Tris buffer, glutamate buffer, acetate buffer, succinate buffer, or histidine buffer. Exemplary buffers include 100 mM glutamate pH 4.5 buffer, 100 mM acetate pH 5 buffer, 100 mM succinate pH 5 buffer, 100 mM phosphate pH 6 buffer, 100 mM histidine pH 6 buffer, 100 mM phosphate pH 6.5 buffer, 100 mM phosphate pH 7.0 buffer, 100 mM histidine pH 7.0 buffer, 100 mM phosphate pH 7.5 buffer, 100 mM Tris pH 7.5 buffer, and 100 mM Tris pH 8.0 buffer. In certain embodiments, GLP-1/glucagon agonist peptides as disclosed are soluble in standard buffers at 0.8 mg/ml over a range of pH, e.g., from pH 4.0 to pH 8.0, e.g., at pH 4.0, 4.5, 5.0, 5.5, 6.0, 6.5, 7.0, 7.5, 8.0, or 8.5. In certain embodiments, GLP-1/glucagon agonist peptides as disclosed are soluble in standard buffers from pH 4.5 to 8.0, 5.0 to 8.0, 5.5 to 8.0, 6.0 to 8.0, 6.5 to 8.0, 7.0 to 8.0, 4.5 to 8.5, 5.5 to 8.5, 5.5 to 8.5, 6.0 to 8.5, 6.5 to 8.5, or 7.0 to 8.5.

In certain embodiments, GLP-1/glucagon agonist peptides as disclosed are formulatable in standard pharmaceutical formulations. Exemplary formulations include, but are not limited to: 0.1M Tris pH 7.5, 150 mM Mannitol, final formulation pH=7.2; 0.05M Tris, 50 mM Arginine/Proline, final formulation pH=8.0; or sodium phosphate buffer (pH8)/1.85% W/V propylene glycol, final formulation pH=7.0. In certain embodiments GLP-1/glucagon agonist peptides as disclosed are soluble is these or other formulations at a concentration up to 0.5 mg/ml, 0.6 mg/ml, 0.7 mg/ml, 0.8 mg/ml, 0.9 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, or more.

In certain embodiments, GLP-1/glucagon agonist peptides as disclosed are acceptably stable against proteases in serum or plasma. Common degradation products of glucagon or GLP-1 include +1 products (acid) and the DPP IV-cleavage products. Products with +1 mass may arise from deamidation at amide groups of glutamine or at the C-terminus. Cleavage products arise from the action of the protease DPP IV in plasma. In certain embodiments, GLP-1/glucagon agonist peptides as disclosed are remain stable in plasma at levels up to 30%, 40%, 50%, 60%, 70%, 80%, 90%, or 100% after 24 hours in plasma at 37° C.

Provided herein is a GLP-1/glucagon agonist peptide comprising the amino acid sequence:

```
                                          (SEQ ID NO: 2)
HX₁X₂GT FTSDX₃ SX₄X₅X₆X₇X₈X₉X₁₀AX₁₁ X₁₂FVX₁₃W
X₁₄X₁₅X₁₆
``` where $X_1$ is S, G, alpha-amino-iso-butyric acid; $X_2$ is Q or E; $X_3$ is Y of K(PEG4palm); $X_4$ is E, R or K(PEG4palm); $X_5$ is Y or K(PEG4palm); $X_6$ is L or K(PEG4palm); $X_7$ is D or E; $X_8$ is S, E or K(PEG4palm); $X_9$ is R, E, S, or K(gEpalm), K(PEG2palm), K(PEG3palm), K(PEG4palm) or K(PEG2-PEG2-gEpalm); $X_{10}$ is R, A, or K(gEpalm), K(PEG4palm); $X_{11}$ is Q, R, A, E or K(gEpalm), K(PEG4palm); $X_{12}$ is D or K(gEpalm); $X_{13}$ is Q, A or E; $X_{14}$ is L or E; $X_{15}$ is V or E; and $X_{16}$ is absent or A (SEQ ID NO:2); wherein only one amino acid is palmitoylated per molecule.

In certain embodiments of the peptides described above, the carboxyl group of $X_{15}$ is pegylated. In some embodiments the PEG group is a polyethylene glycol oligomer of 2, 3, 4, 5, 6, 7, 8, 9, 10, 11 or 12 units. In some embodiments, the $X_{15}$ amino acid is conjugated at the carboxyl end to 6-aminohexanoic acid or 11-aminoundecanoic acid.

In certain embodiments, the isolated peptide comprises an amino acid sequence selected from the group consisting of:

```
                                          (SEQ ID NO: 3)
HSQGTFTSDYSKYLDSRRAQDFVQWLV (SEQ ID NO: 18)
HSQGTFTSDYSKYLDSRRAQDFVQWLE (SEQ ID NO: 4)
HSQGTFTSDYSKYLDKSRARDFVAWLV (SEQ ID NO: 5)
HSQGTFTSDYSKYLDKRRAQDFVQWEV (SEQ ID NO: 6)
HSQGTFTSDYSKYLDKRRAQDFVQWLE (SEQ ID NO: 7)
HSQGTFTSDYSKYLDEKRAQDFVQWLV (SEQ ID NO: 76)
HSQGTFTSDYSKYLDSKRAQDFVQWLV (SEQ ID NO: 77)
HSQGTFTSDYSKYLDSKRARDFVAWLV (SEQ ID NO: 78)
HSQGTFTSDYSKYLDSKRARDFVAWLE (SEQ ID NO: 79)
HSQGTFTSDYSKYLDSKRAQDFVQWLE (SEQ ID NO: 80)
HSQGTFTSDYSKYLDSKRAQDFVQWEV (SEQ ID NO: 81)
HSQGTFTSDKSKYLDSSRARDFVAWLV (SEQ ID NO: 82)
HSQGTFTSDYSKYLDSRKAQDFVQWLE (SEQ ID NO: 3)
HSQGTFTSDYSKYLDSRRAQDFVQWLV (SEQ ID NO: 83)
HSQGTFTSDYSKKLDSSRARDFVAWLV (SEQ ID NO: 84)
HSQGTFTSDYSEYLDSKRAQDFVQWLV (SEQ ID NO: 85)
HSQGTFTSDYSEYLDSKRAADFVQWLV (SEQ ID NO: 86)
HSQGTFTSDYSRYLDSKRARDFVAWLV (SEQ ID NO: 87)
HSQGTFTSDYSKYLDSKRAQDFVAWLV (SEQ ID NO: 76)
HSQGTFTSDYSKYLDSKRAQDFVQWLV (SEQ ID NO: 88)
HSQGTFTSDYSKYKDSRRAQDFVQWLV (SEQ ID NO: 89)
HSQGTFTSDYSKYKDEERAQDFVQWLV (SEQ ID NO: 90)
HSQGTFTSDYSKYKDSSRARDFVAWLV (SEQ ID NO: 14)
HSQGTFTSDYSKYLDSERARDFVAWLV (SEQ ID NO: 91)
HSQGTFTSDYSKYLDKRRAQDFVQWLV (SEQ ID NO: 6)
HSQGTFTSDYSKYLDKRRAQDFVQWLE (SEQ ID NO: 5)
HSQGTFTSDYSKYLDKRRAQDFVQWEV (SEQ ID NO: 92)
HSQGTFTSDYSKYLDSRKAQDFVQWLV (SEQ ID NO: 93)
HSQGTFTSDYSKYLDSRRAKDFVQWLV (SEQ ID NO: 94)
HSQGTFTSDYSKYLDSERAKDFVAWLV (SEQ ID NO: 95)
HSQGTFTSDYSKYLDSRRAQKFVQWLV (SEQ ID NO: 96)
HSEGTFTSDYSKYKDSRRAQDFVQWLV (SEQ ID NO: 97)
HSEGTFTSDYSKYLDSKRAQDFVQWLV (SEQ ID NO: 98)
HGQGTFTSDYSKYLDSKRAQDFVQWLV (SEQ ID NO: 99)
HGQGTFTSDYSKYLDSKRAEDFVQWLV (SEQ ID NO: 100)
HGQGTFTSDYSKYLDSKRAQDFVEWLV (SEQ ID NO: 101)
HGQGTFTSDYSKYLDSEKARDFVAWLV (SEQ ID NO: 102)
HGQGTFTSDYSEYLDSKRAQDFVQWLV (SEQ ID NO: 103)
HGQGTFTSDYSRYLDSKRARDFVEWLV
```

-continued

HGQGTFTSDYSEYLDSKRARDFVEWLV (SEQ ID NO: 104)

HGQGTFTSDYSKYKDSRRAQDFVQWLV (SEQ ID NO: 105)

HGQGTFTSDYSKYLESKRAQDFVQWLV (SEQ ID NO: 106)

HX$_1$QGTFTSDYSKYLDSKRAQDFVAWLV (SEQ ID NO: 107)

HX$_1$QGTFTSDYSKYLDSKRAQDFVQWLV (SEQ ID NO: 108)

HX$_1$QGTFTSDYSKYKDSERARDFVAWLV (SEQ ID NO: 109)

HSQGTFTSDYSKYLDSKRAQDFVQWLEA (SEQ ID NO: 110)

wherein:
$X_1$ is alpha-amino-iso-butyric acid;
when the amino acid at position 10, 13, 14, 16, 17, 18, 20 or 21 is a palmitoylated lysine, then the lysine at position 12 is not palmitoylated;
when the amino acid at position 10, 13, 14, 16, 17, 18, 20 and 21 is not a palmitoylated lysine, then the lysine at position 12 is optionally palmitoylated; and
wherein the peptide is pegylated at the C-terminal amino acid with a (PEG)$x^2$ group, wherein $x^2$ is 2-12.

GLP-1/glucagon agonist peptides provided herein include, but are not limited to the peptides are listed in Table 1 (glucagon is shown for comparative purposes only and does not form part of the invention):

TABLE 1

GLP-1/Glucagon Peptide Sequences

| Peptide | Sequence | SEQ ID NO: |
| --- | --- | --- |
| Glucagon | HSQGTFTSDYSKYLDSRRAQDFVQWLMNT | 1 |
| g357 | HSQGTFTSDYSKYLDSRRAQDFVQWLVX1 | 3 |
| g358 | HSQGTFTSDYSKYLDSRRAQDFVQWLVX2 | 3 |
| g355 | HSQGTFTSDYSKYLDSRRAQDFVQWLVZ2 | 3 |
| g356 | HSQGTFTSDYSKYLDSRRAQDFVQWLVZ4 | 3 |
| g416 | HSQGTFTSDYSBYLDSRRAQDFVQWLVZ4 | 8 |
| g417 | HSQGTFTSDYSB1YLDSRRAQDFVQWLVZ4 | 9 |
| g426 | HSQGTFTSDYSKYBDSRRAQDFVQWLVZ4 | 10 |
| g514 | HGQGTFTSDYSKYBDSRRAQDFVQWLVZ4 | 11 |
| g515 | HSEGTFTSDYSKYBDSRRAQDFVQWLVZ4 | 12 |
| g807 | HSQGTFTSDYSKYBDEERAQDFVQWLVZ4 | 13 |
| g773 | HSQGTFTSDYSKYLDSERARDFVAWLVZ4 | 14 |
| g868 | HX3QGTFTSDYSKYBDSERARDFVAWLVZ4 | 15 |
| g424 | HSQGTFTSDYSKYLDBRRAQDFVQWLVZ4 | 16 |
| g425 | HSQGTFTSDYSKYLDB1RRAQDFVQWLVZ4 | 17 |
| g494 | HSQGTFTSDYSKYLDSRRAQDFVQWLEZ4 | 18 |
| g495 | HSQGTFTSDYSKYLDB1RRAQDFVQWLEZ4 | 19 |

TABLE 1-continued

GLP-1/Glucagon Peptide Sequences

| Peptide | Sequence | SEQ ID NO: |
| --- | --- | --- |
| g496 | HSQGTFTSDYSKYLDBRRAQDFVQWEVZ4 | 20 |
| g497 | HSQGTFTSDYSKYLDB1RRAQDFVQWEVZ4 | 21 |
| g422 | HSQGTFTSDYSKYLDSRBAQDFVQWLVZ4 | 22 |
| g423 | HSQGTFTSDYSKYLDSRB1AQDFVQWLVZ4 | 23 |
| g735 | HGQGTFTSDYSKYLDSEBARDFVAWLVZ4 | 24 |
| g456 | HSQGTFTSDYSKYLDSRRABDFVQWLVZ4 | 25 |
| g457 | HSQGTFTSDYSKYLDSRRAB1DFVQWLVZ4 | 26 |
| g774 | HSQGTFTSDYSKYLDSERABDFVAWLVZ4 | 27 |
| g808 | HSQGTFTSDYSKYLDSRRAQBFVQWLVZ4 | 28 |
| g809 | HSQGTFTSDYSKYLDSRAAQBFVQWLVZ4 | 29 |
| g971 | HSQGTFTSDB1SKYLDSSRARDFVAWLVZ4 | 30 |
| g970 | HSQGTFTSDYSKB1LDSSRARDFVAWLVZ4 | 31 |
| g427 | HSQGTFTSDYSKYB1DSRRAQDFVQWLVZ4 | 32 |
| g969 | HSQGTFTSDYSKYB1DSSRARDFVAWLVZ4 | 33 |
| g972 | HSQGTFTSDYSKYLDB1SRARDFVAWLVZ4 | 34 |
| g414 | HSQGTFTSDYSKYLDSBRAQDFVQWLVZ4 | 35 |
| g415 | HSQGTFTSDYSKYLDSRB1RAQDFVQWLVZ4 | 36 |
| g434 | HSQGTFTSDYSKYLDSB2RAQDFVQWLVZ4 | 37 |
| g435 | HSQGTFTSDYSKYLDSB3RAQDFVQWLVZ4 | 38 |
| g676 | HSQGTFTSDYSEYLDSBRAQDFVQWLVZ4 | 39 |
| g677 | HGQGTFTSDYSEYLDSBRARDFVEWLVZ4 | 40 |
| g500 | HX3QGTFTSDYSKYLDSBRAQDFVQWLVZ4 | 41 |
| g501 | HX3QGTFTSDYSKYLDSB1RAQDFVQWLVZ4 | 42 |
| g430 | HGQGTFTSDYSKYLDSBRAQDFVQWLVZ4 | 43 |
| g431 | HGQGTFTSDYSKYLDSB1RAQDFVQWLVZ4 | 44 |
| g775 | HSQGTFTSDYSEYLDSBRAADFVQWLVZ4 | 45 |
| g719 | HGQGTFTSDYSRYLDSBRARDFVEWLVZ4 | 46 |
| g828 | HSQGTFTSDYSKYLDSBRAQRDFVAWLVZ12 | 47 |
| g827 | HSQGTFTSDYSRYLDSBRARDFVAWLVZ4 | 48 |
| g784 | HSQGTFTSDYSEYLDSBRARDFVAWLVZ4 | 49 |
| g800 | HSQGTFTSDYSKYLDSBRARDFVAWLVZ4 | 50 |
| g966 | HSQGTFTSDYSKYLDSB6RAQDFVQWLEZ4 | 51 |
| g965 | HSQGTFTSDYSKYLDSB5RAQDFVQWLVZ4 | 52 |
| g964 | HSQGTFTSDYSKYLDSB4RAQDFVQWLVZ4 | 53 |
| g870 | HX3QGTFTSDYSKYLDSBRAQDFVAWLVZ4 | 54 |
| g869 | HX3QGTFTSDYSKYLDSBRARDFVAWLVZ4 | 55 |
| g968 | HX3QGTFTSDYSKYLDSB4RARDFVAWLVZ4 | 56 |
| g432 | HSEGTFTSDYSKYLDSBRAQDFVQWLVZ4 | 57 |

TABLE 1-continued

GLP-1/Glucagon Peptide Sequences

| Peptide | Sequence | SEQ ID NO: |
|---|---|---|
| g433 | HSEGTFTSDYSKYLDSB1RAQDFVQWLVZ4 | 58 |
| g498 | HGQGTFTSDYSKYLESBRAQDFVQWLVZ4 | 59 |
| g695 | HGQGTFTSDYSEYLDSBRAQDFVQWLVZ4 | 60 |
| g499 | HGQGTFTSDYSKYLESB1RAQDFVQWLVZ4 | 61 |
| g693 | HGQGTFTSDYSKYLDSBRAEDFVQWLVZ4 | 62 |
| g694 | HGQGTFTSDYSKYLDSBRAQDFVEWLVZ4 | 63 |
| g691 | HGQGTFTSDYSKYLDSBRAQDFVQWLVZ2 | 43 |
| g690 | HGQGTFTSDYSKYLDSBRAQDFVQWLVZ3 | 43 |
| g692 | HGQGTFTSDYSKYLDSBRAQDFVQWLVZ6 | 43 |
| g810 | HSQGTFTSDYSKYLDEBRAQDFVQWLVZ4 | 64 |
| g437 | HSQGTFTSDYSKYLDSB1RAQDFVQWLVZ2 | 65 |
| g436 | HSQGTFTSDYSKYLDSB1RAQDFVQWLVZ3 | 65 |
| g438 | HSQGTFTSDYSKYLDSB1RAQDFVQWLVZ6 | 65 |
| g439 | HSQGTFTSDYSKYLDSB1RAQDFVQWLVZ8 | 65 |
| g440 | HSQGTFTSDYSKYLDSB1RAQDFVQWLVZ12 | 65 |
| g428 | HSQGTFTSDYSKYLDSBRAQDFVQWLEZ4 | 66 |
| g502 | HSQGTFTSDYSKYLDSB3RAQDFVQWLEZ4 | 67 |
| g503 | HSQGTFTSDYSKYLDSB2RAQDFVQWLEZ4 | 68 |
| g429 | HSQGTFTSDYSKYLDSB1RAQDFVQWLEZ4 | 69 |
| g516 | HGQGTFTSDYSKYLDSBRAQDFVQWLEZ4 | 70 |
| g533 | HSQGTFTSDYSKYLDSBRAQDFVQWLEAZ2 | 66 |
| g458 | HSQGTFTSDYSKYLDSBRAQDFVQWEVZ4 | 71 |
| g459 | HSQGTFTSDYSKYLDSB1RAQDFVQWEVZ4 | 72 |
| g533 | HSQGTFTSDYSKYLDSBRAQDFVQWLVZ2 | 35 |
| g454 | HSQGTFTSDYSKYLDSRBAQDFVQWLEZ4 | 73 |
| g455 | HSQGTFTSDYSKYLDSRB1AQDFVQWLEZ4 | 74 |
| g497 | HSQGTFTSDYSKYLDB1RRAQDFVQWEVZ4 | 21 |
| g495 | HSQGTFTSDYSKYLDB1RRAQDFVQWLEZ4 | 19 |
| g967 | HSQGTFTSDYSKYLDSB4RARDFVAWLEZ2 | 75 |

Wherein:
Zx is PEGx; Z2 is PEG2; Z3 is PEG3; Z4 is PEG4; Z6 is PEG6 Z8 is PEG8; Z12 is PEG12;
X1 is 6-aminohexanoic acid; X2 is 11-aminoundecanoic acid; X3 is alpha-amino-iso-butyric acid; B is K(gE-palm); B1 is K(PEG4-palm); B2 is K(PEG3-palm); B3 is K(PEG2-palm); B4 is K(PEG4-gE-palm); B5 is K(PEG2-gE-palm); B6 is K(PEG2-PEG2-gE-palm)
"K(gE-Palm)" refers to a lysine with a palmitoyl group conjugated to the epsilon nitrogen, through a gamma glutamic acid linker.

Methods of Making.

This disclosure provides a method of making a GLP-1/glucagon agonist peptide. GLP-1/glucagon agonist peptides provided herein can be made by any suitable method. For example, in certain embodiments the GLP-1/glucagon agonist peptides provided herein are chemically synthesized by methods well known to those of ordinary skill in the art, e.g., by solid phase synthesis as described by Merrifield (1963, *J. Am. Chem. Soc.* 85:2149-2154). Solid phase peptide synthesis can be accomplished, e.g., by using automated synthesizers, using standard reagents, e.g., as explained in Example 1.

Alternatively, GLP-1/glucagon agonist peptides provided herein can be produced recombinantly using a convenient vector/host cell combination as would be well known to the person of ordinary skill in the art. A variety of methods are available for recombinantly producing GLP-1/glucagon agonist peptides. Generally, a polynucleotide sequence encoding the GLP-1/glucagon agonist peptide is inserted into an appropriate expression vehicle, e.g., a vector which contains the necessary elements for the transcription and translation of the inserted coding sequence. The nucleic acid encoding the GLP-1/glucagon agonist peptide is inserted into the vector in proper reading frame. The expression vector is then transfected into a suitable host cell which will express the GLP-1/glucagon agonist peptide. Suitable host cells include without limitation bacteria, yeast, or mammalian cells. A variety of commercially-available host-expression vector systems can be utilized to express the GLP-1/glucagon agonist peptides described herein.

Modifications, Conjugates, Fusions, and Derivations.

In certain embodiments, GLP-1/glucagon agonist peptides provided herein are stabilized via amino acid modifications. In certain embodiments, the carboxyl group of the C-terminal amino acid is modified by conjugation to 6-aminohexanoic acid or 11-aminoundecanoic acid. In certain embodiments, GLP-1/glucagon agonist peptides are provided in which one or more amino acid residues are acylated. For example, in certain embodiments GLP-1/glucagon agonist peptides provided herein contain one or more lysine residues, in which a palmitoyl moiety is attached to the N (epsilon) group. In certain embodiments a linker is incorporated between lysine and the palmitoyl group. This linker can be a gamma glutamic acid group, or an alternative linker such as, but not limited to, beta alanine and aminohexanoic acid or any of the PEG linkers described herein. Different acylation methods may be used such as addition of cholesterol or myristoyl groups. Alternatively, the linker-palmitoyl moiety could be conjugated to the side chain of cysteine which could be used in place of lysine in the molecules described herein.

Alternatively or in addition, a GLP-1/glucagon agonist peptide as disclosed herein can be associated with a heterologous moiety, e.g., to extend half-life. The heterologous moiety can be a protein, a peptide, a protein domain, a linker, an organic polymer, an inorganic polymer, a polyethylene glycol (PEG), biotin, an albumin, a human serum albumin (HSA), a HSA FcRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, a recombinant polypeptide polymer, a cytokine, and a combination of two or more of such moieties.

For example, GLP-1/glucagon agonist peptides can be fused with a heterologous polypeptide. The peptides can be fused to proteins, either through recombinant gene fusion and expression or by chemical conjugation. Proteins that are suitable as partners for fusion include, without limitation, human serum albumin, antibodies and antibody fragments including fusion to the Fc portion of the antibodies. GLP-1 has been fused to these proteins with retention of potency (L. Baggio et al, *Diabetes* 53 2492-2500 (2004); P. Barrington et al *Diabetes, Obesity and Metabolism* 13 426-433 (2011); P. Paulik et al American Diabetes Association 2012, Poster 1946). Extended recombinant peptide sequences have also been described to give the peptide high molecular mass (V. Schellenberger et al *Nature Biotechnol* 27 1186-1190 (2009); PASylation (EP2173890)). In certain embodiments GLP-1/glucagon agonist peptides are incorporated as the N-terminal part of a fusion protein, with the fusion partner, e.g., the albumin or Fc portion, at the C-terminal end. GLP-1/glucagon agonist peptides as described herein can also be fused to peptides or protein domains, such as 'Albudabs' that have affinity for human serum albumin (M. S. Dennis et al *J Biol Chem* 277 35035-35043 (2002); A. Walker et al Protein Eng Design Selection 23 271-278 (2010)). Methods for fusing a GLP-1/glucagon agonist peptides as disclosed herein with a heterologous polypeptide, e.g., albumin or an Fc region, are well known to those of ordinary skill in the art.

Other heterologous moieties can be conjugated to GLP-1/glucagon agonist peptides to further stabilize or increase half-life. For chemical fusion, certain embodiments feature maintenance of a free N-terminus, but alternative points for derivatization can be made. A further alternative method is to derivatize the peptide with a large chemical moiety such as high molecular weight polyethylene glycol (PEG). A "pegylated GLP-1/glucagon agonist peptide" has a PEG chain covalently bound thereto. Derivatization of GLP-1/ glucagon agonist peptides, e.g., pegylation, can be done at the lysine that is palmitoylated, or alternatively at a residue such as cysteine, that is substituted or incorporated by extension to allow derivatization. GLP-1/glucagon agonist peptide formats above can be characterized in vitro and/or in vivo for relative potency and the balance between GLP-1 and glucagon receptor activation.

The general term "polyethylene glycol chain" or "PEG chain", refers to mixtures of condensation polymers of ethylene oxide and water, in a branched or straight chain, represented by the general formula $H(OCH_2CH_2)_nOH$, where n is an integer of 2, 3, 4, 5, 6, 7, 8, 9, or more. PEG chains include polymers of ethylene glycol with an average total molecular weight selected from the range of about 500 to about 40,000 Daltons. The average molecular weight of a PEG chain is indicated by a number, e.g., PEG-5,000 refers to polyethylene glycol chain having a total molecular weight average of about 5,000.

PEGylation can be carried out by any of the PEGylation reactions known in the art. See, e.g., *Focus on Growth Factors,* 3: 4-10, 1992 and European patent applications EP 0 154 316 and EP 0 401 384. PEGylation may be carried out using an acylation reaction or an alkylation reaction with a reactive polyethylene glycol molecule (or an analogous reactive water-soluble polymer).

Methods for preparing a PEGylated GLP-1/glucagon agonist peptides generally prepared by coupling small amino PEG to a resin and subsequently the other amino acids are coupled sequentially to create the PEGylated peptide. Thus, the steps generally include (a) reacting amino polyethylene glycol with the resin support, and (b) subsequent peptide chain elongation.

Pharmaceutical Compositions

Further provided are compositions, e.g., pharmaceutical compositions, that contain an effective amount of a GLP-1/ glucagon agonist peptide as provided herein, formulated for the treatment of metabolic diseases, e.g., obesity.

Compositions of the disclosure can be formulated according to known methods. Suitable preparation methods are described, for example, in *Remington's Pharmaceutical Sciences,* 19th Edition, A. R. Gennaro, ed., Mack Publishing Co., Easton, Pa. (1995), which is incorporated herein by reference in its entirety. Composition can be in a variety of forms, including, but not limited to an aqueous solution, an emulsion, a gel, a suspension, lyophilized form, or any other form known in the art. In addition, the composition can contain pharmaceutically acceptable additives including, for example, diluents, binders, stabilizers, and preservatives. Once formulated, compositions of the invention can be administered directly to the subject.

Carriers that can be used with compositions of the invention are well known in the art, and include, without limitation, e.g., thyroglobulin, albumins such as human serum albumin, tetanus toxoid, and polyamino acids such as poly L-lysine, poly L-glutamic acid, influenza, hepatitis B virus core protein, and the like. A variety of aqueous carriers can be used, e.g., water, buffered water, 0.8% saline, 0.3% glycine, hyaluronic acid and the like. Compositions can be sterilized by conventional, well known sterilization techniques, or can be sterile filtered. A resulting composition can be packaged for use as is, or lyophilized, the lyophilized preparation being combined with a sterile solution prior to administration. Compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamineoleate, etc.

Method of Treating Obesity, Model Systems.

GLP-1/glucagon agonist peptides can combine the effect of glucagon e.g., inhibition of food intake or regulation of glucose levels with the effect of GLP-1 e.g., inhibition of gastric motility, or promotion of insulin release. They can therefore act to accelerate elimination of excessive adipose tissue, induce sustainable weight loss, and improve glycemic control. GLP-1/glucagon agonist peptides can also act to reduce cardiovascular risk factors such as high cholesterol, and high LDL-cholesterol or abnormal HDL/LDL ratios.

This disclosure provides a method of treating obesity or an obesity-related disease or disorder, comprising administering to a subject in need of treatment a GLP-1/glucagon agonist peptide as disclosed herein. Further provided is a GLP-1/glucagon agonist peptide for treatment of obesity or an obesity-related disease or disorder. Further provided is use of a GLP-1/glucagon agonist peptide as provided herein in the manufacture of a medicament for the treatment of obesity or an obesity-related disease or disorder.

GLP-1/glucagon agonist peptides provided herein can be administered for preventing weight gain, promoting weight loss, reducing excess body weight or treating obesity (e.g. by control of appetite, feeding, food intake, calorie intake, and/or energy expenditure), including morbid obesity. In addition, GLP-1/glucagon agonist peptides provided herein can be used for treatment of other obesity-related metabolic disorders. Examples of other obesity-related disorders include without limitation: insulin resistance, glucose intolerance, pre-diabetes, increased fasting glucose, type 2 diabetes, hypertension, dyslipidemia (or a combination of these metabolic risk factors), glucagonomas, cardiovascular diseases such as congestive heart failure, atherosclerois, arteriosclerosis, coronary heart disease, or peripheral artery disease, stroke, respiratory dysfunction, or renal disease.

"Treatment" is an approach for obtaining beneficial or desired clinical results. As provided herein, beneficial or desired clinical results from the disclosed GLP-1/glucagon agonist peptides include, without limitation, reduced body weight, decreased weight-gain, reduced appetite, reduced or stabilized serum glucose and serum insulin levels, amelioration, palliation, stabilization, diminishment of extent of obesity-related diseases, or a delay or slowing of obesity-related disease progression. "Treatment" refers to both therapeutic treatment and prophylactic or preventative measures in certain embodiments. Those in need of treatment include those already with the disorder as well as those in which the disorder is to be prevented. By treatment is meant inhibiting or reducing an increase in obesity-related symptoms (e.g. weight gain) when compared to the absence of treatment, and is not necessarily meant to imply complete cessation of the relevant condition.

The route of administration of GLP-1/glucagon agonist peptides provided herein can be, for example, oral, parenteral, by inhalation or topical. The term parenteral as used herein includes, e.g., intravenous, intraarterial, intraperitoneal, intramuscular, subcutaneous, rectal, or vaginal administration. Another example of a form for administration is a solution for injection, in particular for intravenous or intraarterial injection or drip. GLP-1/glucagon agonist peptides provided herein can be administered as a single dose or as multiple doses. In certain embodiments, a GLP-1/glucagon agonist peptide is administered by subcutaneous injection.

Parenteral formulations can be a single bolus dose, an infusion or a loading bolus dose followed with a maintenance dose. These compositions can be administered at specific fixed or variable intervals, e.g., once a day, or on an "as needed" basis. Dosage regimens also can be adjusted to provide the optimum desired response (e.g., a therapeutic or prophylactic response).

The amount of a GLP-1/glucagon agonist peptide to be administered can be readily determined by one of ordinary skill in the art without undue experimentation given the disclosure herein. Factors influencing the mode of administration and the respective amount of a GLP-1/glucagon agonist peptide include, but are not limited to, the severity of the disease (e.g., the extent of obesity), the subject's history, and the age, height, weight, health, and physical condition of the subject undergoing therapy. Similarly, the amount of a GLP-1/glucagon agonist peptide to be administered will be dependent upon the mode of administration and whether the subject will undergo a single dose or multiple doses of this agent. In certain embodiments, GLP-1/glucagon agonist peptides provided herein can be administered once per day via injection. In some embodiments, the injection is administered once per week.

Kits

In yet other embodiments, the present disclosure provides kits comprising GLP-1/glucagon agonist peptides, that can be used to perform the methods described herein. In certain embodiments, a kit comprises a GLP-1/glucagon agonist peptide disclosed herein in one or more containers. One skilled in the art will readily recognize that the disclosed GLP-1/glucagon agonist peptides can be readily incorporated into one of the established kit formats which are well known in the art.

EXAMPLES

Example 1: Synthesis, Modifications, and Characterization of GLP-1/Glucagon Agonist Peptides GLP-1/glucagon agonist peptides were synthesized as follows:

A. List of Abbreviations

Ahx: 6-amino hexanoic acid
Aib: alpha-amino iso-butyric acid
Aud 11-amino undecanoic acid
Boc: tert-butyloxycarbonyl
tert-Bu; tert-butyl
DCM: dichloromethane
DIC: diisopropylcarbodiimide
Fmoc: 9-fluorenylmethoxycarbonyl
HOBt: 1-hydroxybenzotriazole
HPLC: High Performance Liquid Chromatography
Mtt: 4-methyltrityl
NMP: N-methylpyrrolidone
palm: palmitic acid
Pbf: 2,2,4,6,7-pentamethyldihydrobenzofuran-5-sulfonyl
TFA: trifluoroacetic acid
TIS: triisopropylsilane
Trt: triphenylmethyl, trityl B. Peptide Synthesis, Purification, and Characterization Elongation of peptide chains on NovaSyn TGR or pre-loaded Fmoc-Wang resin (NovaBiochem) was performed with Prelude solid phase peptide synthesizer (Protein Technologies, Tucson, Ariz., USA). Manufacturer-supplied protocols were applied for coupling of the hydroxybenzotriazole esters of amino acids in N-methylpyrolidone (NMP). The fluorenylmethoxycarbonyl (Fmoc) group was used for the semipermanent protection of amino groups of amino polyethylene glycols and alpha-amino groups of amino acids, whereas the side chains were protected with tert-butyl (tert-Bu) for serine, threonine, aspartic acid, glutamic acid, tyrosine, and 2,2,4,6,7-pentamethyldihydrobenzofuran-5-sulfonyl (Pbf) for arginine, and trityl (Trt) for histidine. The N-terminal amino group of histidine in position 1 was protected with tert-butyloxycarbonyl group (Boc). Lys(Mtt) was incorporated into the peptide chain when a subsequent chemical modification of the side chain was required.

Upon completion of the peptide chain elongation, the Mtt group was removed by treating the peptide-resin with DCM containing 2% TFA and 5% TIS (10×7 ml, each 0.5 min). Coupling of and amino acid, and a PEG linker and a lipid moiety to the side chain of Lys was performed on the Prelude peptide synthesizer using DIC as a coupling reagent in the presence of HOBt.

Peptides were cleaved from the resin using mixture of TFA:TIS:water (95:2.5:2.5). After 2 h at room temperature, the peptidyl resin was filtered, washed with TFA and combined filtrates were evaporated to dryness in vacuo. The residue was triturated with ether, and the precipitate which formed was filtered, washed with ether, and dried. The crude peptides were dissolved in 5% acetic acid in water and analyzed by reverse-phase high-pressure liquid chromatography on a Polaris 3 C8-A column attached to Varian 920-LC system. A standard gradient system of 10 to 90% buffer B over the course of 15 min was used for analysis. Buffer A was 0.1% TFA in water and buffer B was 0.1% TFA in acetonitrile. HPLC profiles were recorded at 210 nm. Preparative separations were performed on Varian ProStar system with a semipreparative C18 RP XBridge Waters column. The above-described solvent system of water and acetonitrile, in a gradient of 30 to 70% buffer B over the course of 30 min, was used for separation. The chromatographically homogeneous products (>97% pure) were analyzed by electrospray mass spectrometry (MassLynx, Waters).

Example 2: In Vitro Studies

Biological Activity of Peptides in Cell-Based cAMP Activity Assay

Peptides are biologically active and may stimulate one or more cellular receptor responses. The biological activity of GLP-1/glucagon agonist peptides synthesized by the method of Example 1 were tested for biological activity, e.g., stimulation of one or more cellular receptor responses, by the following method. Stable cell lines expressing human, mouse, rat, or dog GLP-1 receptor (GLP-1R), glucagon receptor (GCGR) or glucose-dependent insulinotropic peptide (gastric inhibitory polypeptide) receptor (GIPR) were generated in HEK293s or CHO cells by standard methods. Peptide activation of these various receptors results in downstream production of cAMP second messenger which can be measured in a functional activity assay.

A. Assay Method:
Assay Medium:
10% FBS in DMEM (Gibco #41966), containing 0.5 mM IBMX (Sigma #I7018).
Alternative Assay Buffer:
0.1% BSA (Sigma # A3059) in HBSS (with calcium & magnesium), 25 mM HEPES (Gibco #15630), pH7.4 with 0.5 mM IBMX.

Low protein binding 384-well plates (Greiner #781280) were used to perform eleven 1 in 5 serial dilutions of test samples which were made in assay medium. All sample dilutions were made in duplicate.

A frozen cryo-vial of cells expressing the receptor of interest was thawed rapidly in a water-bath, transferred to pre-warmed assay media and spun at 240×g for 5 minutes. Cells were re-suspended in assay media at an optimised concentration (i.e. hGCGr cells at 1×10$^5$ cells/ml, hGLP-1r and hGIPr cells at 0.5×10$^5$ cells/ml).

From the dilution plate, a 5 mcL replica was stamped onto a black shallow-well u-bottom 384-well plate (Corning #3676). To this, 5 mcL cell suspension was added and the plates incubated at room temperature for 30 minutes.

cAMP levels were measured using a commercially available cAMP dynamic 2 HTRF kit (Cisbio, Cat #62AM4PEJ), following the two step protocol as per manufacturer's recommendations. In brief; anti-cAMP cryptate (donor fluorophore) and cAMP-d2 (acceptor fluorophore) were made up separately by diluting each 1/20 in conjugate & lysis buffer provided in the kit. 5 mcL anti-cAMP cryptate was added to all wells of the assay plate, and 5 mcL cAMP-d2 added to all wells except non-specific binding (NSB) wells, to which conjugate & lysis buffer was added. Plates were incubated at room temperature for one hour and then read on an Envision (Perkin Elmer) using excitation wavelength of 320 nm and emission wavelengths of 620 nm & 665 nm.

% Delta F values were calculated for each well as follows:

$$\% \text{ Delta } F(\Delta F) = \frac{(\text{Sample } A665/A620 \text{ ratio} - \text{NSB } A665/A620 \text{ ratio})}{(\text{NSB } A665/A620 \text{ ratio})} \times 100$$

Media only wells (non-specific binding (NSB)) were used as background for the % Delta F calculations. Data was subsequently analysed using Data Processor software, with 4-parameter logistical analysis and graphed as % activation plots; from this EC50 values for each sample were obtained. Assay window is defined by Negative control (cells plus both HTRF reagents giving Total Binding) as basal cell cAMP levels and Positive control defined by the maximal response caused by Reference Ligand Control (e.g. cells plus ligand (e.g. GLP-1) and both HTRF reagents).

$EC_{50}$ refers to the half maximal effective concentration, defined as a concentration which induces a response halfway between basal and maximum response. Serial dilution of a peptide sample may produce a dose response curve, from which an $EC_{50}$ value can be determined. The lower the $EC_{50}$ the better the potency of the test sample.

The synthesized GLP-1/glucagon agonist peptides and their EC50 values determined in cAMP assays, are shown in Table 2.

TABLE 2 cAMP activity of additional GLP-1/glucagon agonist peptides

| | GLP1 $EC_{50}$ nM | Glcg $EC_{50}$ nM | Palmitoylation | C-terminus | Other substitutions |
|---|---|---|---|---|---|
| glucagon | | 0.003 | | | |
| g357 | 1.6 | 0.08 | | LV-Ahx | |
| g358 | 3.2 | 0.03 | | LV-Aud | |
| g355 | 0.67 | 0.03 | | LV(PEG)2 | |
| g356 | 0.05 | 0.12 | | LV(PEG)4 | |
| g416 | 1 | 0.6 | K(gEpalm)12 | LV(PEG4) | |
| g807 | 1.4 | 0.01 | K(gEpalm)14 | LV(PEG4) | E16, E17 |
| g773, 799 | 0.04 | 0.08 | K(gEpalm)14 | LV(PEG4) | R20 A24 E17 |
| g868 | 0.014 | 0.02 | K(gEpalm)14 | LV(PEG4) | R20 A24, E17 Aib2 |
| g426 | 0.124 | 0.003 | K(gEpalm)14 | LV(PEG4) | |
| g514 | 0.1 | 0.02 | K(gEpalm)14 | LV(PEG4) | G2 |
| g515 | 0.1 | 0.4 | K(gEpalm)14 | LV(PEG4) | E3 |
| g424 | 0.4 | 0.009 | K(gEpalm)16 | LV(PEG4) | |
| g494 | 4 | 0.002 | K(gEpalm)16 | LE(PEG4) | |
| g496 | 8 | 24 | K(gEpalm)16 | EV(PEG4) | |

TABLE 2-continued cAMP activity of additional GLP-1/glucagon agonist peptides

| | GLP1 EC$_{50}$ nM | Glcg EC$_{50}$ nM | Palmitoylation | C-terminus | Other substitutions |
|---|---|---|---|---|---|
| g422 | 0.2 | 0.7 | K(gEpalm)18 | LV(PEG4) | |
| g735 | 0.8 | >1800 | K(gEpalm)18 | LV(PEG4) | R20 A24 E17 G2 |
| g456 | 1.3 | 0.07 | K(gEpalm)20 | LV(PEG4) | |
| g774 | 35 | 2.3 | K(gEpalm)20 | LV(PEG4) | E17 A24 |
| g808 | 50 | 0.12 | K(gEpalm)21 | LV(PEG4) | |
| g809 | 0.43 | 0.07 | K(gEpalm)21 | LV(PEG4) | A18 |
| g971 | 0.015 | 0.007 | K(PEG4palm)10 | LV(PEG4) | R20 A24 S17 |
| g417 | 0.02 | 0.003 | K(PEG4palm)12 | LV(PEG4) | |
| g970 | 0.014 | 0.003 | K(PEG4palm)13 | LV(PEG4) | R20 A24 S17 |
| g427 | 0.004 | 0.002 | K(PEG4palm)14 | LV(PEG4) | |
| g969 | 0.01 | 0.006 | K(PEG4palm)14 | LV(PEG4) | R20 A24 S17 |
| g425 | 0.008 | 0.002 | K(PEG4palm)16 | LV(PEG4) | |
| g495 | 0.09 | 0.002 | K(PEG4palm)16 | LE(PEG4) | |
| g497 | 15 | 0.3 | K(PEG4palm)16 | EV(PEG4) | |
| g972 | 0.03 | 0.03 | K(PEG4palm)16 | LV(PEG4) | R20 A24 S17 |
| g423 | 0.01 | 0.004 | K(PEG4palm)18 | LV(PEG4) | |
| g457 | 0.03 | 0.004 | K(PEG4palm)20 | LV(PEG4) | |
| g414 | 0.2 | 0.016 | K(gEpalm)17 | LV(PEG4) | |
| g676 | 1.2 | 40 | K(gEpalm)17 | LV(PEG4) | E12 |
| g677 | 0.3 | 25 | K(gEpalm)17 | LV(PEG4), | E12 R20 E24, G2 |
| g500 | 0.08 | 0.16 | K(gEpalm)17 | LV(PEG4) | Aib2 |
| g430 | 0.35 | 0.8 | K(gEpalm)17 | LV(PEG4) | G2 |
| g775 | 0.23 | 0.08 | K(gEpalm)17 | LV(PEG4) | A20 E24 |
| g719 | 0.09 | 0.75 | K(gEpalm)17 | LV(PEG4) | R20 E24, R12, G2 |
| g828 | 0.04 | 0.02 | K(gEpalm)17 | LV(PEG12) | R20 A24, R12 |
| g827 | 0.2 | 0.04 | K(gEpalm)17 | LV(PEG4) | R20 A24, R12 |
| g784 | 0.3 | 1.5 | K(gEpalm)17 | LV(PEG4) | R20 A24, E12 |
| g800 | 0.09 | 0.014 | K(gEpalm)17 | LV(PEG4) | R20 A24 |
| g870 | 0.09 | 11 | K(gEpalm)17 | LV(PEG4) | A24, Aib2 |
| g869 | 0.11 | 0.065 | K(gEpalm)17 | LV(PEG4) | R20 A24, Aib2 |
| g432 | 0.07 | 2.2 | K(gEpalm)17 | LV(PEG4) | E3 |
| g498 | 0.6 | 2 | K(gEpalm)17 | LV(PEG4) | G2, E15 |
| g695, 676 | 0.2 | 4 | K(gEpalm)17 | LV(PEG4) | G2 E12 |
| g693 | 0.1 | >2 | K(gEpalm)17 | LV(PEG4) | G2, E20 |
| g694 | 0.07 | 0.2 | K(gEpalm)17 | LV(PEG4) | G2, E24 |
| g691 | 0.05 | 0.13 | K(gEpalm)17 | LV(PEG2) | G2 |
| g690 | 0.06 | 0.1 | K(gEpalm)17 | LV(PEG3) | G2 |
| g692 | 0.06 | 0.13 | K(gEpalm)17 | LV(PEG6) | G2 |
| g810 | 0.5 | 0.03 | K(gEpalm)17 | LV(PEG4) | E16 |
| g415 | 0.007 | 0.002 | K(PEG4palm)17 | LV(PEG4) | |
| g431 | 0.006 | 0.004 | K(PEG4palm)17 | LV(PEG4) | G2 |
| g501 | 0.03 | 0.003 | K(PEG4palm)17 | LV(PEG4) | Aib2 |
| g433 | 0.004 | 0.03 | K(PEG4palm)17 | LV(PEG4) | E3 |
| g499 | 0.02 | 0.03 | K(PEG4palm)17 | LV(PEG4) | G2 E15 |
| g966 | 0.012 | 0.001 | K(PEG2, PEG2, gEpalm)17 | LE(PEG4) | R20 A24 |
| g965 | 0.017 | 0.002 | K(PEG2, gEpalm)17 | LV(PEG4) | R20 A24 |
| g964 | 0.015 | 0.002 | K(PEG4, gEpalm)17 | LV(PEG4) | R20 A24 |
| g968 | 0.025 | 0.006 | K(PEG4, gEpalm)17 | LV(PEG4) | R20 A24 Aib2 |
| g434 | 0.005 | 0.02 | K(PEG3palm)17 | LV(PEG4) | |
| g435 | 0.01 | 0.002 | K(PEG2palm)17 | LV(PEG4) | |
| g437 | 0.006 | 0.002 | K(PEG4palm)17 | LV(PEG2) | |
| g436 | 0.01 | 0.002 | K(PEG4palm)17 | LV(PEG3) | |
| g438 | 0.005 | 0.002 | K(PEG4palm)17 | LV(PEG6) | |
| g439 | 0.008 | 0.002 | K(PEG4palm)17 | LV(PEG8) | |
| g440 | 0.008 | 0.002 | K(PEG4palm)17 | LV(PEG12) | |
| g428 | 0.2 | 0.003 | K(gEpalm)17 | LE(PEG4) | |
| g516 | 0.6 | 0.08 | K(gEpalm)17 | LE(PEG4) | G2 |
| g533 | 0.09 | 0.003 | K(gEpalm)17 | LEA(PEG2) | |
| g458 | 0 | 9 | K(gEpalm)17 | EV(PEG4) | |
| g533 | 0.09 | 0.003 | K(gEpalm)17 | LEA(PEG2) | |
| g454 | 0.5 | 0.08 | K(gEpalm)18 | LE(PEG4) | |
| g497 | 15 | 0.3 | K(PEG4palm)16 | EV(PEG4) | |
| g495 | 0.09 | 0.002 | K(PEG4palm)16 | LE(PEG4) | |
| g429 | 0.004 | 0.005 | K(PEG4palm)17 | LE(PEG4) | |
| g503 | 0.02 | 0.002 | K(PEG3palm)17 | LE(PEG4) | |

TABLE 2-continued cAMP activity of additional GLP-1/glucagon agonist peptides

|      | GLP1 EC$_{50}$ nM | Glcg EC$_{50}$ nM | Palmitoylation | C-terminus | Other substitutions |
|------|-------------------|-------------------|----------------|------------|---------------------|
| g502 | 0.03              | 0.001             | K(PEG2palm)17  | LE(PEG4)   |                     |
| g459 | 14                | 0.3               | K(PEG4palm)17  | EV(PEG4)   |                     |
| g967 | 0.016             | 0.006             | K(PEG4gEpalm)17| LE(PEG2)   | R20 A24 E27         |
| g455 | 0.012             | 0.001             | K(PEG4palm)18  | LE(PEG4)   |                     |

Abbreviations:
K(gE-palm) = Lysine with a palmitoyl group conjugated to the epsilon nitrogen, through a gamma glutamic acid linker;
Aib, alpha-amino-iso-butyric acid.
K(PEG,palm) = Lysine conjugated with x number of PEG units and a palmitoyl group at the epsilon nitrogen. Substitutions noted are with respect to the following amino acid sequence: HSQGTFTSDYSKYLDSRRAQDFVQW + C-terminal amino acids indicated The disclosure is not to be limited in scope by the specific embodiments described which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. An isolated peptide comprising:
   HX$_1$QGTFTSDYSKYLDSB$_4$RARDFVAWLV
   (OCH$_2$CH$_2$)$_4$ (SEQ ID NO:56)
   wherein:
   X$_1$ is alpha-amino-iso-butyric acid; and
   B$_4$ is K((OCH$_2$CH$_2$)$_4$-gE-palm).

2. A pharmaceutical composition comprising the peptide of claim 1 and a pharmaceutically acceptable carrier.

3. A kit comprising the composition of claim 2.

4. An isolated peptide consisting of:
   HX$_1$QGTFTSDYSKYLDSB$_4$RARDFVAWLV
   (OCH$_2$CH$_2$)$_4$(SEQ ID NO:56),
   wherein:
   X$_1$ is alpha-amino-iso-butyric acid; and
   B$_4$ is K((OCH$_2$CH$_2$)$_4$-gE-palm).

5. A pharmaceutical composition comprising the peptide of claim 4 and a pharmaceutically acceptable carrier.

6. A kit comprising the composition of claim 5.

* * * * *

```
                        SEQUENCE LISTING

<160> NUMBER OF SEQ ID NOS: 110

<210> SEQ ID NO 1
<211> LENGTH: 29
<212> TYPE: PRT
<213> ORGANISM: Artificial Sequence
<220> FEATURE:
<223> OTHER INFORMATION: Synthetic Glucagon Analogue

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 28
<212> TYPE: PRT
<213> ORGANISM: Artificial Sequence
<220> FEATURE:
<223> OTHER INFORMATION: Synthetic Glucagon analogue
<220> FEATURE:
<221> NAME/KEY: MOD_RES
<222> LOCATION: (2)..(2)
<223> OTHER INFORMATION: S, G or Aib
<220> FEATURE:
<221> NAME/KEY: misc_feature
<222> LOCATION: (3)..(3)
<223> OTHER INFORMATION: Q or E
<220> FEATURE:
<221> NAME/KEY: misc_feature
<222> LOCATION: (10)..(10)
<223> OTHER INFORMATION: Y or K(PEG4palm)
<220> FEATURE:
<221> NAME/KEY: misc_feature
<222> LOCATION: (12)..(12)
<223> OTHER INFORMATION: E, R, K or K(PEG4palm)
<220> FEATURE:
<221> NAME/KEY: misc_feature
<222> LOCATION: (13)..(13)
<223> OTHER INFORMATION: Y or K(PEG4palm)
<220> FEATURE:
<221> NAME/KEY: misc_feature
<222> LOCATION: (14)..(14)
<223> OTHER INFORMATION: L or K(PEG4palm)
```

```
<220> FEATURE:
<221> NAME/KEY: misc_feature
<222> LOCATION: (15)..(15)
<223> OTHER INFORMATION: D or E
<220> FEATURE:
<221> NAME/KEY: misc_feature
<222> LOCATION: (16)..(16)
<223> OTHER INFORMATION: S, E or K(PEG4palm)
<220> FEATURE:
<221> NAME/KEY: misc_feature
<222> LOCATION: (17)..(17)
<223> OTHER INFORMATION: R, E, S, K(gEpalm), K(PEG2palm), K(PEG3palm),
      K(PEG4palm) or K(PEG2-PEG2-gEpalm)
<220> FEATURE:
<221> NAME/KEY: misc_feature
<222> LOCATION: (18)..(18)
<223> OTHER INFORMATION: R, A, or K(gEpalm), K(PEG4palm)
<220> FEATURE:
<221> NAME/KEY: misc_feature
<222> LOCATION: (20)..(20)
<223> OTHER INFORMATION: Q, R, A, E or KgEpalm), K(PEG4palm);
<220> FEATURE:
<221> NAME/KEY: misc_feature
<222> LOCATION: (21)..(21)
<223> OTHER INFORMATION: D or K(gEpalm)
<220> FEATURE:
<221> NAME/KEY: misc_feature
<222> LOCATION: (24)..(24)
<223> OTHER INFORMATION: Q, A or E
<220> FEATURE:
<221> NAME/KEY: misc_feature
<222> LOCATION: (26)..(26)
<223> OTHER INFORMATION: L or E
<220> FEATURE:
<221> NAME/KEY: misc_feature
<222> LOCATION: (27)..(27)
<223> OTHER INFORMATION: V or E
<220> FEATURE:
<221> NAME/KEY: misc_feature
<222> LOCATION: (28)..(28)
<223> OTHER INFORMATION: absent or A

<400> SEQUENCE: 2

His Xaa Xaa Gly Thr Phe Thr Ser Asp Xaa Ser Xaa Xaa Xaa Xaa
1               5                   10                  15

Xaa Xaa Ala Xaa Xaa Phe Val Xaa Trp Xaa Xaa Xaa
            20                  25

<210> SEQ ID NO 3
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Val
            20                  25

<210> SEQ ID NO 4
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 4

His Ser Gln Gly Thr Phe Thr Ser Asp Tyr Ser Lys Tyr Leu Asp Lys
1               5                   10                  15
```

```
Ser Arg Ala Arg Asp Phe Val Ala Trp Leu Val
            20                  25

<210> SEQ ID NO 5
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 5

His Ser Gln Gly Thr Phe Thr Ser Asp Tyr Ser Lys Tyr Leu Asp Lys
1               5                   10                  15

Arg Arg Ala Gln Asp Phe Val Gln Trp Glu Val
            20                  25

<210> SEQ ID NO 6
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 6

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Glu
            20                  25

<210> SEQ ID NO 7
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 7

His Ser Gln Gly Thr Phe Thr Ser Asp Tyr Ser Lys Tyr Leu Asp Glu
1               5                   10                  15

Lys Arg Ala Gln Asp Phe Val Gln Trp Leu Val
            20                  25

<210> SEQ ID NO 8
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (12)..(12)
<223> OTHER INFORMATION: K(gE-palm)

<400> SEQUENCE: 8

His Ser Gln Gly Thr Phe Thr Ser Asp Tyr Ser Xaa Tyr Leu Asp Ser
1               5                   10                  15

Arg Arg Ala Gln Asp Phe Val Gln Trp Leu Val
            20                  25

<210> SEQ ID NO 9
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
```

```
<221> NAME/KEY: MISC_FEATURE
<222> LOCATION: (12)..(12)
<223> OTHER INFORMATION: K(PEG4-palm)

<400> SEQUENCE: 9

His Ser Gln Gly Thr Phe Thr Ser Asp Tyr Ser Xaa Tyr Leu Asp Ser
1               5                   10                  15

Arg Arg Ala Gln Asp Phe Val Gln Trp Leu Val
            20                  25

<210> SEQ ID NO 10
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (14)..(14)
<223> OTHER INFORMATION: K(gE-palm)

<400> SEQUENCE: 10

His Ser Gln Gly Thr Phe Thr Ser Asp Tyr Ser Lys Tyr Xaa Asp Ser
1               5                   10                  15

Arg Arg Ala Gln Asp Phe Val Gln Trp Leu Val
            20                  25

<210> SEQ ID NO 11
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (14)..(14)
<223> OTHER INFORMATION: K(gE-palm)

<400> SEQUENCE: 11

His Gly Gln Gly Thr Phe Thr Ser Asp Tyr Ser Lys Tyr Xaa Asp Ser
1               5                   10                  15

Arg Arg Ala Gln Asp Phe Val Gln Trp Leu Val
            20                  25

<210> SEQ ID NO 12
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (14)..(14)
<223> OTHER INFORMATION: K(gE-palm)

<400> SEQUENCE: 12

His Ser Glu Gly Thr Phe Thr Ser Asp Tyr Ser Lys Tyr Xaa Asp Ser
1               5                   10                  15

Arg Arg Ala Gln Asp Phe Val Gln Trp Leu Val
            20                  25

<210> SEQ ID NO 13
<211> LENGTH: 27
<212> TYPE: PRT
<213> ORGANISM: Artificial Sequence
<220> FEATURE:
<223> OTHER INFORMATION: Synthetic Glucagon Analogue
```

```
<220> FEATURE:
<221> NAME/KEY: MISC_FEATURE
<222> LOCATION: (14)..(14)
<223> OTHER INFORMATION: K(gE-palm)

<400> SEQUENCE: 13

His Ser Gln Gly Thr Phe Thr Ser Asp Tyr Ser Lys Tyr Xaa Asp Glu
1               5                   10                  15

Glu Arg Ala Gln Asp Phe Val Gln Trp Leu Val
            20                  25

<210> SEQ ID NO 14
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 14

His Ser Gln Gly Thr Phe Thr Ser Asp Tyr Ser Lys Tyr Leu Asp Ser
1               5                   10                  15

Glu Arg Ala Arg Asp Phe Val Ala Trp Leu Val
            20                  25

<210> SEQ ID NO 15
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (14)..(14)
<223> OTHER INFORMATION: K(gE-palm)

<400> SEQUENCE: 15

His Xaa Gln Gly Thr Phe Thr Ser Asp Tyr Ser Lys Tyr Xaa Asp Ser
1               5                   10                  15

Glu Arg Ala Arg Asp Phe Val Ala Trp Leu Val
            20                  25

<210> SEQ ID NO 16
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (16)..(16)
<223> OTHER INFORMATION: K(gE-palm)

<400> SEQUENCE: 16

His Ser Gln Gly Thr Phe Thr Ser Asp Tyr Ser Lys Tyr Leu Asp Xaa
1               5                   10                  15

Arg Arg Ala Gln Asp Phe Val Gln Trp Leu Val
            20                  25

<210> SEQ ID NO 17
<211> LENGTH: 27
<212> TYPE: PRT
<213> ORGANISM: Artificial Sequence
<220> FEATURE:
```

```
<223> OTHER INFORMATION: Synthetic glucagon analogue
<220> FEATURE:
<221> NAME/KEY: MISC_FEATURE
<222> LOCATION: (16)..(16)
<223> OTHER INFORMATION: K(PEG4-palm);

<400> SEQUENCE: 17

His Ser Gln Gly Thr Phe Thr Ser Asp Tyr Ser Lys Tyr Leu Asp Xaa
1               5                   10                  15

Arg Arg Ala Gln Asp Phe Val Gln Trp Leu Val
            20                  25

<210> SEQ ID NO 18
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 18

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Glu
            20                  25

<210> SEQ ID NO 19
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (16)..(16)
<223> OTHER INFORMATION: K(PEG4-palm)

<400> SEQUENCE: 19

His Ser Gln Gly Thr Phe Thr Ser Asp Tyr Ser Lys Tyr Leu Asp Xaa
1               5                   10                  15

Arg Arg Ala Gln Asp Phe Val Gln Trp Leu Glu
            20                  25

<210> SEQ ID NO 20
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (16)..(16)
<223> OTHER INFORMATION: K(gE-palm)

<400> SEQUENCE: 20

His Ser Gln Gly Thr Phe Thr Ser Asp Tyr Ser Lys Tyr Leu Asp Xaa
1               5                   10                  15

Arg Arg Ala Gln Asp Phe Val Gln Trp Glu Val
            20                  25

<210> SEQ ID NO 21
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
```

<222> LOCATION: (16)..(16)
<223> OTHER INFORMATION: K(PEG4-palm)

<400> SEQUENCE: 21

His Ser Gln Gly Thr Phe Thr Ser Asp Tyr Ser Lys Tyr Leu Asp Xaa
1               5                   10                  15

Arg Arg Ala Gln Asp Phe Val Gln Trp Glu Val
            20                  25

<210> SEQ ID NO 22
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (18)..(18)
<223> OTHER INFORMATION: K(gE-palm)

<400> SEQUENCE: 22

His Ser Gln Gly Thr Phe Thr Ser Asp Tyr Ser Lys Tyr Leu Asp Ser
1               5                   10                  15

Arg Xaa Ala Gln Asp Phe Val Gln Trp Leu Val
            20                  25

<210> SEQ ID NO 23
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (18)..(18)
<223> OTHER INFORMATION: K(PEG4-palm)

<400> SEQUENCE: 23

His Ser Gln Gly Thr Phe Thr Ser Asp Tyr Ser Lys Tyr Leu Asp Ser
1               5                   10                  15

Arg Xaa Ala Gln Asp Phe Val Gln Trp Leu Val
            20                  25

<210> SEQ ID NO 24
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (18)..(18)
<223> OTHER INFORMATION: K(gE-palm)

<400> SEQUENCE: 24

His Gly Gln Gly Thr Phe Thr Ser Asp Tyr Ser Lys Tyr Leu Asp Ser
1               5                   10                  15

Glu Xaa Ala Arg Asp Phe Val Ala Trp Leu Val
            20                  25

<210> SEQ ID NO 25
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:

```
<221> NAME/KEY: MISC_FEATURE
<222> LOCATION: (20)..(20)
<223> OTHER INFORMATION: K(gE-palm)

<400> SEQUENCE: 25

His Ser Gln Gly Thr Phe Thr Ser Asp Tyr Ser Lys Tyr Leu Asp Ser
1               5                   10                  15

Arg Arg Ala Xaa Asp Phe Val Gln Trp Leu Val
            20                  25

<210> SEQ ID NO 26
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (20)..(20)
<223> OTHER INFORMATION: K(PEG4-palm)

<400> SEQUENCE: 26

His Ser Gln Gly Thr Phe Thr Ser Asp Tyr Ser Lys Tyr Leu Asp Ser
1               5                   10                  15

Arg Arg Ala Xaa Asp Phe Val Gln Trp Leu Val
            20                  25

<210> SEQ ID NO 27
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (20)..(20)
<223> OTHER INFORMATION: K(gE-palm)

<400> SEQUENCE: 27

His Ser Gln Gly Thr Phe Thr Ser Asp Tyr Ser Lys Tyr Leu Asp Ser
1               5                   10                  15

Glu Arg Ala Xaa Asp Phe Val Ala Trp Leu Val
            20                  25

<210> SEQ ID NO 28
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (21)..(21)
<223> OTHER INFORMATION: K(gE-palm)

<400> SEQUENCE: 28

His Ser Gln Gly Thr Phe Thr Ser Asp Tyr Ser Lys Tyr Leu Asp Ser
1               5                   10                  15

Arg Arg Ala Gln Xaa Phe Val Gln Trp Leu Val
            20                  25

<210> SEQ ID NO 29
<211> LENGTH: 27
<212> TYPE: PRT
<213> ORGANISM: Artificial Sequence
<220> FEATURE:
<223> OTHER INFORMATION: Synthetic Glucagon Analogue
```

```
<220> FEATURE:
<221> NAME/KEY: MISC_FEATURE
<222> LOCATION: (21)..(21)
<223> OTHER INFORMATION: K(gE-palm)

<400> SEQUENCE: 29

His Ser Gln Gly Thr Phe Thr Ser Asp Tyr Ser Lys Tyr Leu Asp Ser
1               5                   10                  15

Arg Ala Ala Gln Xaa Phe Val Gln Trp Leu Val
            20                  25

<210> SEQ ID NO 30
<211> LENGTH: 27
<212> TYPE: PRT
<213> ORGANISM: Artificial Sequence
<220> FEATURE:
<223> OTHER INFORMATION: Synthetic Glugagon Analogue
<220> FEATURE:
<221> NAME/KEY: MISC_FEATURE
<222> LOCATION: (10)..(10)
<223> OTHER INFORMATION: K(PEG4-palm)

<400> SEQUENCE: 30

His Ser Gln Gly Thr Phe Thr Ser Asp Xaa Ser Lys Tyr Leu Asp Ser
1               5                   10                  15

Ser Arg Ala Arg Asp Phe Val Ala Trp Leu Val
            20                  25

<210> SEQ ID NO 31
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (13)..(13)
<223> OTHER INFORMATION: K(PEG4-palm)

<400> SEQUENCE: 31

His Ser Gln Gly Thr Phe Thr Ser Asp Tyr Ser Lys Xaa Leu Asp Ser
1               5                   10                  15

Ser Arg Ala Arg Asp Phe Val Ala Trp Leu Val
            20                  25

<210> SEQ ID NO 32
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (14)..(14)
<223> OTHER INFORMATION: K(PEG4-palm)

<400> SEQUENCE: 32

His Ser Gln Gly Thr Phe Thr Ser Asp Tyr Ser Lys Tyr Xaa Asp Ser
1               5                   10                  15

Arg Arg Ala Gln Asp Phe Val Gln Trp Leu Val
            20                  25

<210> SEQ ID NO 33
<211> LENGTH: 27
<212> TYPE: PRT
<213> ORGANISM: Artificial Sequence
<220> FEATURE:
```

```
<223> OTHER INFORMATION: Synthetic Glucagon Analogue
<220> FEATURE:
<221> NAME/KEY: MISC_FEATURE
<222> LOCATION: (16)..(16)
<223> OTHER INFORMATION: K(gE-palm)

<400> SEQUENCE: 33

His Ser Gln Gly Thr Phe Thr Ser Asp Tyr Ser Lys Tyr Leu Asp Xaa
1               5                   10                  15

Ser Arg Ala Arg Asp Phe Val Ala Trp Leu Val
            20                  25

<210> SEQ ID NO 34
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (16)..(16)
<223> OTHER INFORMATION: K(PEG4-palm)

<400> SEQUENCE: 34

His Ser Gln Gly Thr Phe Thr Ser Asp Tyr Ser Lys Tyr Leu Asp Xaa
1               5                   10                  15

Ser Arg Ala Arg Asp Phe Val Ala Trp Leu Val
            20                  25

<210> SEQ ID NO 35
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 35

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Val
            20                  25

<210> SEQ ID NO 36
<211> LENGTH: 28
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (18)..(18)
<223> OTHER INFORMATION: K(PEG4-palm)

<400> SEQUENCE: 36

His Ser Gln Gly Thr Phe Thr Ser Asp Tyr Ser Lys Tyr Leu Asp Ser
1               5                   10                  15

Arg Xaa Arg Ala Gln Asp Phe Val Gln Trp Leu Val
            20                  25

<210> SEQ ID NO 37
<211> LENGTH: 27
<212> TYPE: PRT
<213> ORGANISM: Artificial Sequence
```

```
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG3-palm)

<400> SEQUENCE: 37

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Val
            20                  25

<210> SEQ ID NO 38
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG2-palm)

<400> SEQUENCE: 38

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Val
            20                  25

<210> SEQ ID NO 39
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 39

His Ser Gln Gly Thr Phe Thr Ser Asp Tyr Ser Glu Tyr Leu Asp Ser
1               5                   10                  15

Xaa Arg Ala Gln Asp Phe Val Gln Trp Leu Val
            20                  25

<210> SEQ ID NO 40
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 40

His Gly Gln Gly Thr Phe Thr Ser Asp Tyr Ser Glu Tyr Leu Asp Ser
1               5                   10                  15

Xaa Arg Ala Arg Asp Phe Val Glu Trp Leu Val
            20                  25

<210> SEQ ID NO 41
<211> LENGTH: 27
<212> TYPE: PRT
```

```
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: K(gE-palm)

<400> SEQUENCE: 41

His Xaa Gln Gly Thr Phe Thr Ser Asp Tyr Ser Lys Tyr Leu Asp Ser
1               5                   10                  15

Xaa Arg Ala Gln Asp Phe Val Gln Trp Leu Val
            20                  25

<210> SEQ ID NO 42
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: K(PEG4-palm)

<400> SEQUENCE: 42

His Xaa Gln Gly Thr Phe Thr Ser Asp Tyr Ser Lys Tyr Leu Asp Ser
1               5                   10                  15

Xaa Arg Ala Gln Asp Phe Val Gln Trp Leu Val
            20                  25

<210> SEQ ID NO 43
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 43

His Gly Gln Gly Thr Phe Thr Ser Asp Tyr Ser Lys Tyr Leu Asp Ser
1               5                   10                  15

Xaa Arg Ala Gln Asp Phe Val Gln Trp Leu Val
            20                  25

<210> SEQ ID NO 44
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG4-palm

<400> SEQUENCE: 44

His Gly Gln Gly Thr Phe Thr Ser Asp Tyr Ser Lys Tyr Leu Asp Ser
```

```
1               5                   10                  15
Xaa Arg Ala Gln Asp Phe Val Gln Trp Leu Val
            20                  25

<210> SEQ ID NO 45
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 45

His Ser Gln Gly Thr Phe Thr Ser Asp Tyr Ser Glu Tyr Leu Asp Ser
1               5                   10                  15

Xaa Arg Ala Ala Asp Phe Val Gln Trp Leu Val
            20                  25

<210> SEQ ID NO 46
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 46

His Gly Gln Gly Thr Phe Thr Ser Asp Tyr Ser Arg Tyr Leu Asp Ser
1               5                   10                  15

Xaa Arg Ala Arg Asp Phe Val Glu Trp Leu Val
            20                  25

<210> SEQ ID NO 47
<211> LENGTH: 28
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 47

His Ser Gln Gly Thr Phe Thr Ser Asp Tyr Ser Lys Tyr Leu Asp Ser
1               5                   10                  15

Xaa Arg Ala Gln Arg Asp Phe Val Ala Trp Leu Val
            20                  25

<210> SEQ ID NO 48
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 48
```

His Ser Gln Gly Thr Phe Thr Ser Asp Tyr Ser Arg Tyr Leu Asp Ser
1               5                   10                  15

Xaa Arg Ala Arg Asp Phe Val Ala Trp Leu Val
            20                  25

<210> SEQ ID NO 49
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 49

His Ser Gln Gly Thr Phe Thr Ser Asp Tyr Ser Glu Tyr Leu Asp Ser
1               5                   10                  15

Xaa Arg Ala Arg Asp Phe Val Ala Trp Leu Val
            20                  25

<210> SEQ ID NO 50
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 50

His Ser Gln Gly Thr Phe Thr Ser Asp Tyr Ser Lys Tyr Leu Asp Ser
1               5                   10                  15

Xaa Arg Ala Arg Asp Phe Val Ala Trp Leu Val
            20                  25

<210> SEQ ID NO 51
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG2-PEG2-gE-palm)

<400> SEQUENCE: 51

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Glu
            20                  25

<210> SEQ ID NO 52
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG2-gE-palm)

<400> SEQUENCE: 52

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Val
            20                  25

<210> SEQ ID NO 53
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG4-gE-palm)

<400> SEQUENCE: 53

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Val
            20                  25

<210> SEQ ID NO 54
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: K(gE-palm)

<400> SEQUENCE: 54

His Xaa Gln Gly Thr Phe Thr Ser Asp Tyr Ser Lys Tyr Leu Asp Ser
1               5                   10                  15

Xaa Arg Ala Gln Asp Phe Val Ala Trp Leu Val
            20                  25

<210> SEQ ID NO 55
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: K(gE-palm)

<400> SEQUENCE: 55

His Xaa Gln Gly Thr Phe Thr Ser Asp Tyr Ser Lys Tyr Leu Asp Ser
1               5                   10                  15

Xaa Arg Ala Arg Asp Phe Val Ala Trp Leu Val
            20                  25

<210> SEQ ID NO 56
<211> LENGTH: 27
<212> TYPE: PRT

```
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: K(PEG4-gE-palm)

<400> SEQUENCE: 56

His Xaa Gln Gly Thr Phe Thr Ser Asp Tyr Ser Lys Tyr Leu Asp Ser
1               5                   10                  15

Xaa Arg Ala Arg Asp Phe Val Ala Trp Leu Val
            20                  25

<210> SEQ ID NO 57
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 57

His Ser Glu Gly Thr Phe Thr Ser Asp Tyr Ser Lys Tyr Leu Asp Ser
1               5                   10                  15

Xaa Arg Ala Gln Asp Phe Val Gln Trp Leu Val
            20                  25

<210> SEQ ID NO 58
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG4-palm)

<400> SEQUENCE: 58

His Ser Glu Gly Thr Phe Thr Ser Asp Tyr Ser Lys Tyr Leu Asp Ser
1               5                   10                  15

Xaa Arg Ala Gln Asp Phe Val Gln Trp Leu Val
            20                  25

<210> SEQ ID NO 59
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 59

His Gly Gln Gly Thr Phe Thr Ser Asp Tyr Ser Lys Tyr Leu Glu Ser
1               5                   10                  15

Xaa Arg Ala Gln Asp Phe Val Gln Trp Leu Val
            20                  25
```

<210> SEQ ID NO 60
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 60

His Gly Gln Gly Thr Phe Thr Ser Asp Tyr Ser Glu Tyr Leu Asp Ser
1               5                   10                  15

Xaa Arg Ala Gln Asp Phe Val Gln Trp Leu Val
            20                  25

<210> SEQ ID NO 61
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG4-palm)

<400> SEQUENCE: 61

His Gly Gln Gly Thr Phe Thr Ser Asp Tyr Ser Lys Tyr Leu Glu Ser
1               5                   10                  15

Xaa Arg Ala Gln Asp Phe Val Gln Trp Leu Val
            20                  25

<210> SEQ ID NO 62
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG4-palm)

<400> SEQUENCE: 62

His Gly Gln Gly Thr Phe Thr Ser Asp Tyr Ser Lys Tyr Leu Asp Ser
1               5                   10                  15

Xaa Arg Ala Glu Asp Phe Val Gln Trp Leu Val
            20                  25

<210> SEQ ID NO 63
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 63

His Gly Gln Gly Thr Phe Thr Ser Asp Tyr Ser Lys Tyr Leu Asp Ser
1               5                   10                  15

Xaa Arg Ala Gln Asp Phe Val Glu Trp Leu Val 20                  25

<210> SEQ ID NO 64
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 64

His Ser Gln Gly Thr Phe Thr Ser Asp Tyr Ser Lys Tyr Leu Asp Glu
1               5                   10                  15

Xaa Arg Ala Gln Asp Phe Val Gln Trp Leu Val
            20                  25

<210> SEQ ID NO 65
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG4-palm)

<400> SEQUENCE: 65

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Val
            20                  25

<210> SEQ ID NO 66
<211> LENGTH: 28
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 66

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Glu Ala
            20                  25

<210> SEQ ID NO 67
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG2-palm)

<400> SEQUENCE: 67

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Glu
            20                  25

<210> SEQ ID NO 68
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG3-palm)

<400> SEQUENCE: 68

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Glu
            20                  25

<210> SEQ ID NO 69
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG4-palm)

<400> SEQUENCE: 69

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Glu
            20                  25

<210> SEQ ID NO 70
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 70

His Gly Gln Gly Thr Phe Thr Ser Asp Tyr Ser Lys Tyr Leu Asp Ser
1               5                   10                  15

Xaa Arg Ala Gln Asp Phe Val Gln Trp Leu Glu
            20                  25

<210> SEQ ID NO 71
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(gE-palm)

<400> SEQUENCE: 71

His Ser Gln Gly Thr Phe Thr Ser Asp Tyr Ser Lys Tyr Leu Asp Ser
1               5                   10                  15

```
Xaa Arg Ala Gln Asp Phe Val Gln Trp Glu Val
        20                  25

<210> SEQ ID NO 72
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG4-palm)

<400> SEQUENCE: 72

His Ser Gln Gly Thr Phe Thr Ser Asp Tyr Ser Lys Tyr Leu Asp Ser
1               5                   10                  15

Xaa Arg Ala Gln Asp Phe Val Gln Trp Glu Val
        20                  25

<210> SEQ ID NO 73
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (18)..(18)
<223> OTHER INFORMATION: K(gE-palm)

<400> SEQUENCE: 73

His Ser Gln Gly Thr Phe Thr Ser Asp Tyr Ser Lys Tyr Leu Asp Ser
1               5                   10                  15

Arg Xaa Ala Gln Asp Phe Val Gln Trp Leu Glu
        20                  25

<210> SEQ ID NO 74
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (18)..(18)
<223> OTHER INFORMATION: K(PEG4-palm)

<400> SEQUENCE: 74

His Ser Gln Gly Thr Phe Thr Ser Asp Tyr Ser Lys Tyr Leu Asp Ser
1               5                   10                  15

Arg Xaa Ala Gln Asp Phe Val Gln Trp Leu Glu
        20                  25

<210> SEQ ID NO 75
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (17)..(17)
<223> OTHER INFORMATION: K(PEG4-gE-palm)

<400> SEQUENCE: 75

His Ser Gln Gly Thr Phe Thr Ser Asp Tyr Ser Lys Tyr Leu Asp Ser
```

```
                1               5                   10                  15
Xaa Arg Ala Arg Asp Phe Val Ala Trp Leu Glu
            20                  25

<210> SEQ ID NO 76
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 76

His Ser Gln Gly Thr Phe Thr Ser Asp Tyr Ser Lys Tyr Leu Asp Ser
1               5                   10                  15

Lys Arg Ala Gln Asp Phe Val Gln Trp Leu Val
            20                  25

<210> SEQ ID NO 77
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 77

His Ser Gln Gly Thr Phe Thr Ser Asp Tyr Ser Lys Tyr Leu Asp Ser
1               5                   10                  15

Lys Arg Ala Arg Asp Phe Val Ala Trp Leu Val
            20                  25

<210> SEQ ID NO 78
<211> LENGTH: 27
<212> TYPE: PRT
<213> ORGANISM: Artificial Sequence
<220> FEATURE:
<223> OTHER INFORMATION: Synthetic Glucagon Analgue

<400> SEQUENCE: 78

His Ser Gln Gly Thr Phe Thr Ser Asp Tyr Ser Lys Tyr Leu Asp Ser
1               5                   10                  15

Lys Arg Ala Arg Asp Phe Val Ala Trp Leu Glu
            20                  25

<210> SEQ ID NO 79
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 79

His Ser Gln Gly Thr Phe Thr Ser Asp Tyr Ser Lys Tyr Leu Asp Ser
1               5                   10                  15

Lys Arg Ala Gln Asp Phe Val Gln Trp Leu Glu
            20                  25

<210> SEQ ID NO 80
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 80
```

```
His Ser Gln Gly Thr Phe Thr Ser Asp Tyr Ser Lys Tyr Leu Asp Ser
1               5                   10                  15

Lys Arg Ala Gln Asp Phe Val Gln Trp Glu Val
            20                  25

<210> SEQ ID NO 81
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 81

His Ser Gln Gly Thr Phe Thr Ser Asp Lys Ser Lys Tyr Leu Asp Ser
1               5                   10                  15

Ser Arg Ala Arg Asp Phe Val Ala Trp Leu Val
            20                  25

<210> SEQ ID NO 82
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 82

His Ser Gln Gly Thr Phe Thr Ser Asp Tyr Ser Lys Tyr Leu Asp Ser
1               5                   10                  15

Arg Lys Ala Gln Asp Phe Val Gln Trp Leu Glu
            20                  25

<210> SEQ ID NO 83
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 83

His Ser Gln Gly Thr Phe Thr Ser Asp Tyr Ser Lys Lys Leu Asp Ser
1               5                   10                  15

Ser Arg Ala Arg Asp Phe Val Ala Trp Leu Val
            20                  25

<210> SEQ ID NO 84
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 84

His Ser Gln Gly Thr Phe Thr Ser Asp Tyr Ser Glu Tyr Leu Asp Ser
1               5                   10                  15

Lys Arg Ala Gln Asp Phe Val Gln Trp Leu Val
            20                  25

<210> SEQ ID NO 85
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 85
```

His Ser Gln Gly Thr Phe Thr Ser Asp Tyr Ser Arg Tyr Leu Asp Ser
1               5                   10                  15

Lys Arg Ala Arg Asp Phe Val Ala Trp Leu Val
            20                  25

<210> SEQ ID NO 86
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 86

His Ser Gln Gly Thr Phe Thr Ser Asp Tyr Ser Arg Tyr Leu Asp Ser
1               5                   10                  15

Lys Arg Ala Arg Asp Phe Val Ala Trp Leu Val
            20                  25

<210> SEQ ID NO 87
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 87

His Ser Gln Gly Thr Phe Thr Ser Asp Tyr Ser Lys Tyr Leu Asp Ser
1               5                   10                  15

Lys Arg Ala Gln Asp Phe Val Ala Trp Leu Val
            20                  25

<210> SEQ ID NO 88
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 88

His Ser Gln Gly Thr Phe Thr Ser Asp Tyr Ser Lys Tyr Lys Asp Ser
1               5                   10                  15

Arg Arg Ala Gln Asp Phe Val Gln Trp Leu Val
            20                  25

<210> SEQ ID NO 89
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 89

His Ser Gln Gly Thr Phe Thr Ser Asp Tyr Ser Lys Tyr Lys Asp Glu
1               5                   10                  15

Glu Arg Ala Gln Asp Phe Val Gln Trp Leu Val
            20                  25

<210> SEQ ID NO 90
<211> LENGTH: 27
<212> TYPE: PRT
<213> ORGANISM: Artificial Sequence
<220> FEATURE:
<223> OTHER INFORMATION: Synthetic Glucagon Analogue

```
<400> SEQUENCE: 90

His Ser Gln Gly Thr Phe Thr Ser Asp Tyr Ser Lys Tyr Lys Asp Ser
1               5                   10                  15

Ser Arg Ala Arg Asp Phe Val Ala Trp Leu Val
            20                  25

<210> SEQ ID NO 91
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 91

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Val
            20                  25

<210> SEQ ID NO 92
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 92

His Ser Gln Gly Thr Phe Thr Ser Asp Tyr Ser Lys Tyr Leu Asp Ser
1               5                   10                  15

Arg Lys Ala Gln Asp Phe Val Gln Trp Leu Val
            20                  25

<210> SEQ ID NO 93
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 93

His Ser Gln Gly Thr Phe Thr Ser Asp Tyr Ser Lys Tyr Leu Asp Ser
1               5                   10                  15

Arg Arg Ala Lys Asp Phe Val Gln Trp Leu Val
            20                  25

<210> SEQ ID NO 94
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 94

His Ser Gln Gly Thr Phe Thr Ser Asp Tyr Ser Lys Tyr Leu Asp Ser
1               5                   10                  15

Glu Arg Ala Lys Asp Phe Val Ala Trp Leu Val
            20                  25

<210> SEQ ID NO 95
<211> LENGTH: 27
<212> TYPE: PRT
<213> ORGANISM: Artificial Sequence
<220> FEATURE:
<223> OTHER INFORMATION: Synthetic Glucagon Analogue
```

<400> SEQUENCE: 95

His Ser Gln Gly Thr Phe Thr Ser Asp Tyr Ser Lys Tyr Leu Asp Ser
1               5                   10                  15

Arg Arg Ala Gln Lys Phe Val Gln Trp Leu Val
            20                  25

<210> SEQ ID NO 96
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 96

His Ser Glu Gly Thr Phe Thr Ser Asp Tyr Ser Lys Tyr Lys Asp Ser
1               5                   10                  15

Arg Arg Ala Gln Asp Phe Val Gln Trp Leu Val
            20                  25

<210> SEQ ID NO 97
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 97

His Ser Glu Gly Thr Phe Thr Ser Asp Tyr Ser Lys Tyr Leu Asp Ser
1               5                   10                  15

Lys Arg Ala Gln Asp Phe Val Gln Trp Leu Val
            20                  25

<210> SEQ ID NO 98
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 98

His Gly Gln Gly Thr Phe Thr Ser Asp Tyr Ser Lys Tyr Leu Asp Ser
1               5                   10                  15

Lys Arg Ala Gln Asp Phe Val Gln Trp Leu Val
            20                  25

<210> SEQ ID NO 99
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 99

His Gly Gln Gly Thr Phe Thr Ser Asp Tyr Ser Lys Tyr Leu Asp Ser
1               5                   10                  15

Lys Arg Ala Glu Asp Phe Val Gln Trp Leu Val
            20                  25

<210> SEQ ID NO 100
<211> LENGTH: 27
<212> TYPE: PRT
<213> ORGANISM: Artificial Sequence
<220> FEATURE:

<223> OTHER INFORMATION: Synthetic Glucagon Analogue

<400> SEQUENCE: 100

His Gly Gln Gly Thr Phe Thr Ser Asp Tyr Ser Lys Tyr Leu Asp Ser
1               5                   10                  15

Lys Arg Ala Gln Asp Phe Val Glu Trp Leu Val
            20                  25

<210> SEQ ID NO 101
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 101

His Gly Gln Gly Thr Phe Thr Ser Asp Tyr Ser Lys Tyr Leu Asp Ser
1               5                   10                  15

Glu Lys Ala Arg Asp Phe Val Ala Trp Leu Val
            20                  25

<210> SEQ ID NO 102
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 102

His Gly Gln Gly Thr Phe Thr Ser Asp Tyr Ser Glu Tyr Leu Asp Ser
1               5                   10                  15

Lys Arg Ala Gln Asp Phe Val Gln Trp Leu Val
            20                  25

<210> SEQ ID NO 103
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 103

His Gly Gln Gly Thr Phe Thr Ser Asp Tyr Ser Arg Tyr Leu Asp Ser
1               5                   10                  15

Lys Arg Ala Arg Asp Phe Val Glu Trp Leu Val
            20                  25

<210> SEQ ID NO 104
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 104

His Gly Gln Gly Thr Phe Thr Ser Asp Tyr Ser Glu Tyr Leu Asp Ser
1               5                   10                  15

Lys Arg Ala Arg Asp Phe Val Glu Trp Leu Val
            20                  25

<210> SEQ ID NO 105
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 105

His Gly Gln Gly Thr Phe Thr Ser Asp Tyr Ser Lys Tyr Lys Asp Ser
1               5                   10                  15

Arg Arg Ala Gln Asp Phe Val Gln Trp Leu Val
            20                  25

<210> SEQ ID NO 106
<211> LENGTH: 27
<212> TYPE: PRT
<213> ORGANISM: Artificial Sequence
<220> FEATURE:
<223> OTHER INFORMATION: Synthetic Glucagon Analogue

<400> SEQUENCE: 106

His Gly Gln Gly Thr Phe Thr Ser Asp Tyr Ser Lys Tyr Leu Glu Ser
1               5                   10                  15

Lys Arg Ala Gln Asp Phe Val Gln Trp Leu Val
            20                  25

<210> SEQ ID NO 107
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (2)..(2)
<223> OTHER INFORMATION: Aib

<400> SEQUENCE: 107

His Xaa Gln Gly Thr Phe Thr Ser Asp Tyr Ser Lys Tyr Leu Asp Ser
1               5                   10                  15

Lys Arg Ala Gln Asp Phe Val Ala Trp Leu Val
            20                  25

<210> SEQ ID NO 108
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (2)..(2)
<223> OTHER INFORMATION: Aib

<400> SEQUENCE: 108

His Xaa Gln Gly Thr Phe Thr Ser Asp Tyr Ser Lys Tyr Leu Asp Ser
1               5                   10                  15

Lys Arg Ala Gln Asp Phe Val Gln Trp Leu Val
            20                  25

<210> SEQ ID NO 109
<211> LENGTH: 27
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (2)..(2)
<223> OTHER INFORMATION: Aib

```
<400> SEQUENCE: 109

His Xaa Gln Gly Thr Phe Thr Ser Asp Tyr Ser Lys Tyr Lys Asp Ser
1               5                   10                  15

Glu Arg Ala Arg Asp Phe Val Ala Trp Leu Val
            20                  25

<210> SEQ ID NO 110
<211> LENGTH: 28
<212> TYPE: PRT
<213> ORGANISM: Artificial Sequence
<220> FEATURE:
<223> OTHER INFORMATION: Synthetic Glucagon Analogue

<400> SEQUENCE: 110

His Ser Gln Gly Thr Phe Thr Ser Asp Tyr Ser Lys Tyr Leu Asp Ser
1               5                   10                  15

Lys Arg Ala Gln Asp Phe Val Gln Trp Leu Glu Ala
            20                  25
```